United States Patent [19]
Miyamoto et al.

[11] Patent Number: 6,015,835
[45] Date of Patent: Jan. 18, 2000

[54] METHODS OF INDUCING ANALGESIA OR ANESTHESIA AND TREATING OR PREVENTING ISCHEMIC INJURY OF TISSUES IN GENERAL

[75] Inventors: Tadaomi Miyamoto, Kitakyushu; Koho Miyamoto, Okinawa-ken, both of Japan

[73] Assignee: Meddiss, Incorporated, Fukuoka, Japan

[21] Appl. No.: 09/028,482

[22] Filed: Feb. 24, 1998

Related U.S. Application Data

[63] Continuation-in-part of application No. 08/622,606, Mar. 26, 1996, abandoned.

[51] Int. Cl.$^7$ ................................................ A01N 37/12
[52] U.S. Cl. ........................... 514/562; 514/578; 514/665
[58] Field of Search ..................................... 514/578, 665, 514/82

[56] References Cited

U.S. PATENT DOCUMENTS

| | | | |
|---|---|---|---|
| 5,084,007 | 1/1992 | Malin et al. | 604/20 |
| 5,084,482 | 1/1992 | Hirsch et al. | 514/562 |

FOREIGN PATENT DOCUMENTS 2 051 789   1/1981   United Kingdom .

OTHER PUBLICATIONS

Schrader et al., Adenosine and Adenine Nucleotides as Regulators of Cellular Function, "Intracellular pathways involved in the formation of adenosin", 1995, pp. 5–13.

Rudolphi et al., Cerebrovascular and Brain Metabolism Reviews, vol. 4, 1992, pp. 346–369, "Adenosine and Brain Ischemia".

Lehmann et al., Neuroscience Letters, vol. 52, 1984, pp. 341–346, "A role for taurine in the maintenance of homeostasis in the central nervous system during yperexcitation".

Schubert et al., Acta Neurochir, vol. 57(Suppl.), 1993, pp. 80–88, "Cerebral protection by Adenosine".

S. Budavari, The Merck Index, 11$^{th}$ Edition, p. 943, entry 5896 and pp. 1433–1434, entry 9043, 1989, "Methitural".

J.E.F. Reynolds, Martindale, The Extra Pharmacopoeia, 29$^{th}$ Edition, pp. 843 and 1621, 1989, "Methionine and Racemethionine" and "Taurine".

Chemical Abstracts of Japan, vol. 96, No. 155452e, Ruggero G. Fariello, et al., Neurology, vol. 32, pp. 241, Mar. 1982, "Homotaurine (3 Aminopropanesulfonic Acid, 3APS) Protects Form the Convulsant and Cytotoxic Effect of Systemically Administered Kainic Acid".

Henrik Hagberg et al, "Ischemia–Induced Shift of Inhibitory and Excitatory Amino Acids from Intra– to Extracellular Compartments", *Journal of Cerebral Blood Flow and Metabolism*, vol. 5, No. 1, Mar. 1985, pp. 413–419, XP000675093.

Henrik Hagberg et al, "Extracellular overflow of glutamate, aspartate, GABA and taurine in the cortex and basal ganglia of fetal lambs during hypoxia–ischemia", *Neuroscience Letters*, vol. 78, No. 3, Aug. 1987, pp. 311–317, XP000675088.

D. Lekieffre et al, "Concomitant increases in the extracellular concentrations of excitatory and inhibitory amino acids in the rat hippocampus during forebrain ischemia", *Neuroscience Letters*, vol. 137, 1992, pp. 78–82, XP000677297.

David W. Busija et al, "Dilator effects of amino acid neurotransmitters on piglet pial arterioles", *American Journal of Physiology*, vol. 257, No. 4, Part 2, Oct. 1989, pp. H1200–H1203, XP000675109.

Carl S. Hornfeldt et al, "Antinociceptive Effects of Intrathecal Taurine and Calcium in the Mouse", *Life Sciences*, vol. 50, No. 24, 1992, pp. 1925–1934, XP000675107.

David B. Masters et al, "Release of amino acids into regional superfusates of the spinal cord by mechano stimulation of the reproductive tract", *Brain Research*, vol. 621, No. 2, 1993, pp. 279–290, XP000675094.

David H. Smullin et al, "Interactions between substance P, calcitonin gene–related peptide, taurine and excitatory amino acids in the spinal cord", *Pain*, vol. 42, No. 1, 1990, pp. 93–101, XP000675202.

Carlos Beyer et al, "Blockage of Substance P–Induced Scratching Behavior in Rats by the Intrathecal Administration of Inhibitory Amino Acid Agonists", *Pharmacology Biochemistry and Behavior*, vol. 34, No. 3, 1989, pp. 491–495, XP000677502.

Carlos Beyer et al, "Prevention of the Convulsant and Hyperalgesic Action of Strychnine by Intrathecal Glycine and Related Amino Acids", *Pharmacology Biochemistry and Behavior*, vol. 29, No. 1, 1988, pp. 73–78, XP000677503.

Avital Schurr et al, "Pharmacological Protection Against Cerebral Hypoxia by Taurine in vitro", *Elsevier Science Publishers B.V.*, 1986, pp. 363–370, XP000677851.

*Primary Examiner*—Dwayne C. Jones
*Attorney, Agent, or Firm*—Oblon, Spivak, McClelland, Maier & Neustadt, P.C.

[57] ABSTRACT

The invention relates to methods for inducing analgesia (or even anesthesia) and for prevention or amelioration of damage caused by ischemic or traumatic injury of tissues in general, but especially neural, for the central nervous system being the most vulnerable of all tissues, by the systemic administration of a therapeutically effective amount of primarily taurine, and secondarily homotaurine and/or methionine for a sufficient period of time (several hours to a few days, depending on the severity of the injury, and timing when therapy is initiated from the time of injury) to allow recovery from the original insult or from phenomena that follow the initial injury.

12 Claims, 7 Drawing Sheets

METHODS OF INDUCING ANALGESIA OR ANESTHESIA AND TREATING OR PREVENTING ISCHEMIC INJURY OF TISSUES IN GENERAL

This is a continuation-in-part application of U.S. patent application Ser. No. 08/622,606, filed Mar. 26, 1996 and abandoned on Apr. 20, 1999.

BACKGROUND ART

1. Field of the Invention

This invention is applicable in all fields of medicine, but more particularly, in the specialties of anesthesiology, neurology, neurosurgery, internal medicine, pediatrics, oncology, obstetrics, neo-natology, cardiology, cardiac surgery, radiology, critical care medicine and transplantation in general. It relates to the use of exogenous taurine, homotaurine or methionine either alone or in various combinations but generally including taurine to induce analgesia or even anesthesia, or to protect organs in general and particularly the central nervous system (CNS) in patients (in-vivo conditions), or explanted donor organs (including but not limited to the liver, pancreas, small bowel, lungs, kidneys or the heart) (in vitro conditions) to be used for transplantation from the ravaging effects of hypoxia or ischemia (lack of or decreased oxygenation or blood flow) caused by vascular severance, such as during organ harvesting for transplantation, primary or secondary intra-vascular obstructions (such as in stroke) or extra-vascular factors accompanying trauma to the tissue (head trauma or during neurosurgical procedures).

2. Conventional Art

CNS ischemia is characterized by a complex cascade of hemodynamic, electrophysiological and biochemical processes with many interwoven vicious circles. The decrease of CNS blood flow below a critical threshold results in energy failure, tissue acidosis, disturbed ion homeostasis characterized by enhanced cellular $K^+$ efflux and $Na^+$ and $Ca^{++}$ influx, membrane depolarization and cytotoxic edema (Choi, 1990; Rudolphi, 1992; Wieloch, 1982). These basic biochemical processes of ischemia might be quantitatively different in various organs but are qualitatively common to practically all tissues, and therefore general principles aimed to prevent or ameliorate them could be extended to organs other than the CNS.

In the CNS it has been reported that extracellular or interstitial levels of the excitatory aminoacids (EAAs) as well as inhibitory and potentially protective aminoacids such as taurine increase 4–20 fold during or shortly after ischemic injury (Benveniste, 1984; Hillered, 1989; Simpson, 1992) or head trauma (Nilsson, 1990; Persson, 1992); likewise there is a similar outpour of adenosine (Nilsson, 1990; Van Wylen, 1986). The flooding of the extracellular space with EAAs results in indiscriminate and continuous activation of postsynaptic EAAs receptors (phenomenon known as excitotoxicity) such as those for NMDA (N-methyl-D-aspartate, activated by glutamate and aspartate), AMPA (alpha-amino-3-hydroxy-5-methyl-4-isoxazole propionic acid) and KA (kainate) which may result in ultimate cell death, an occurrence that may be delayed for 2 or 3 days or even longer. This elevation of (interstitial) extracellular EAAs levels is thought to be part of the periphenomena of most acute CNS injury events leading to cell damage (Choi, 1990; DeLeo, 1987; Rothman, 1986). Even though the exact physiopathologic role glycine plays is not fully known, for NMDA receptors to become fully activated seems to require the presence of glycine in addition to the EAAs (glutamate or aspartate) (Johnson, 1987).

The role and importance of adenosine receptors in general and particularly in the CNS have been recently reviewed by Fredholm (1995) and Jacobson (1995). The neuroprotective role of adenosine in cerebral ischemia have been summarized by Choi (1990), Rudolphi (1992) and Schubert (1993).

Purinergic compounds which may interact with these adenosine receptors include the naturally present adenosine and adenosine tri-phosphate (ATP) or the synthetic adenosine analogues, and are well known to exert multiple functions in almost every tissue of the body, but are particularly conspicuous and therefore have been extensively studied in the brain where general antinociceptive (analgesic or even anesthetic), antiepileptic and tissue protective effects are well documented. Even though all the mechanisms of action of adenosine are not completely elucidated, the general consensus, as has been reviewed and summarized by Fredholm (1995) is that the effects are mediated by receptors of mainly the A1 (considered to be sensitive to $\mu$molar concentrations of adenosine and functionally to produce hyperpolarization of membranes and inhibition of the release of EAAs) and A2 types, (sensitive to mmolar concentrations, and functionally characterized to produce release rather than inhibition of EAAs on one hand but particularly dilatation of the vasculature) located in cell membranes on the cell surface. In the CNS, although there are areas rich in A2 type receptors, A1 are predominant (Fredholm, 1995; Jacobson, 1995), and consequently their activation induce mostly widespread inhibition of the release of EAAs.

Pharmacological manipulation of these adenosine effects has been described as adenosinergic approach, and may include the administration of adenosine itself or ATP, or metabolically stable synthetic adenosine analogues, or therapy directed to increasing tissular adenosine concentration either by inhibiting its reuptake by the cells, or by inhibiting the destruction of the endogenously formed adenosine, or by the administration of precursors or pro-drugs of adenosine to enhance its endogenous production.

The exogenous administration of purinergic compounds (adenosine or its analogues and ATP) that act on the adenosine receptors or pharmacological agents that alter the tissue levels of endogenous adenosine have been proven to have important antinociceptive: sedative, analgesic (Fukunaga, 1995; Sollevi, 1992), antiepileptic and/or neuroprotective activities (Fredholm, 1995; Rudolphi, 1992, Schubert, 1993). Because the extent of protection obtained with adenosinergic approaches in experimentally induced ischemia conditions of the CNS and other tissues, seems to be dose-dependent (Goldberg, 1988), in seeking significant A1 receptors effects, the administration of sufficient adenosinergic agents will almost always result in A2 receptors activation (dangerous levels of hypotension) and these consequent cardiovascular effects have hindered the acceptance of the adenosinergic approach at any clinical level (anesthesia, neurology or transplantation field) (Rudolphi, 1992).

In spite of the extensive work and considerable knowledge gained on the physiology and pharmacology of the various adenosine receptors as well as the adenosine analogues which were developed with the idea of selectively activating A1 receptors at small adenosine concentrations, to avoid the cardiovascular (vasodilating) hypotensive effects, which are mainly the result of A2 receptors activation that occurs at greater concentrations, many of the adenosinergic approaches affect both types of the ubiquitous and widely distributed adenosine receptors (throughout the entire body). Consequently their use has been hampered mainly by the undesirable cardiovascular effects, i.e., severe and dangerous decrease of blood pressure (hypotension) when dosages sufficient to attain adequate tissue levels at the target organ are used.

Until now, the beneficial CNS effects of adenosine and adenosinergic approaches in regards to antinociception and neuroprotection have been explained on the basis of the general effects of hyperpolarization of membranes and inhibition of the release of EAAs, effects that are thought to be mediated mainly by A1 type Adenosine receptors, but the inventors have further uncovered the heretofore non-described effect that adenosine releases in a dose-dependent manner various inhibitory aminoacids but mainly taurine, regardless of the area of the brain, whether rich in A1 or A2 receptors and therefore suggesting that such effects might not be mediated by the classic Adenosine receptors.

Although how taurine functions is not fully understood as yet, taurine is particularly abundant in the retina (where light promotes oxidation) and the brain (where oxidation might destroy the CNS function). Taurine is known to be a naturally present aminoacid with important anticalcic, antioxidant and protective features (Huxtable, 1980; Lehmann A., 1984; Wright C. E. 1986). Indeed, exogenously administered taurine in cats (van Gelder, 1972,a; 1976,b) as well as homotaurine in rats (Fariello, 1982) were reported previously to have antiepileptic effects but never found their way to be used as therapeutic agents. The common denominator of a number of protective pharmacological agents including barbiturates, benzodiazepines, isoflurane (all with anesthetic and anticonvulsant properties) and anticonvulsants (such as MK 801) is precisely the anticonvulsant action when used in therapeutically effective doses, and typically they induce marked EEG quiescence or functional depression (Kato, 1990; McDonald, 1990; Michenfelder [a], 1988). The inventors have further demonstrated that exogeneously administered taurine could mimic many if not all of the effects elicited by systemic administration of purinergic compounds, including those of anti-nociception with minimal or no cardiovascular effects.

The role of adenosine in pain perception as antinociceptive was summarized by Fredholm (1995). Of particular interest is the fact that the analgesic effects of morphine and morphine-like narcotics seem to be exerted via stimulation of adenosine release (Stone, 1981), and those of benzodiazepines via inhibition of adenosine uptake mechanisms. The administration of intravenous adenosine (Sollevi, 1992) or ATP (which is degraded to adenosine at the tissue level) proved to markedly decrease the requirements for anesthetic agents (Fukunaga, 1994) transoperatively, and notably the requirements for postoperative analgesics (Sollevi, 1992).

SUMMARY OF THE INVENTION

This invention is therefore aimed at solving the above-mentioned shortcoming of adenosinergic approaches, while obtaining either analgesic (anesthetic) or protective effects, thus providing similar or even greater beneficial effects than adenosinergic approaches without the troublesome hypotension.

Exogenous purinergic compounds delivered directly in the brain tissue via microdyalisis probes (thus avoiding hypotension that plagues systemic administration) (a well known technique for those skilled in the art of drug delivery for pharmacological studies and analysis of interstitial fluid levels of various substances including aminoacids) induces the release of a number of inhibitory aminoacids but especially taurine into the CNS interstitial space. Therefore the logical conclusion is that some of the beneficial effects so far ascribed to adenosine could be actually due to this taurine, which is known to have important inhibitory, anticalcic and antioxidant activities, for which it has been described as the natural protective substance (Huxtable, 1980; Wright, 1986).

Ischemic injury involves $Ca^{++}$ overload of cells and subsequent oxidation of lipid membrane and cytoskeleton structures; this phenomenon is particularly conspicuous in the excitable CNS tissue (Wieloch, 1982). The anticalcic and antioxidant effects of taurine have been shown in the retina and various neural preparations (cultures, slices, synaptosomes) as well as in cardiac tissue, thus establishing the grounds for extending the protective effects to tissues other than the CNS as well, for the treatment or prevention of ischemic injury of a variety of organs.

For metabolic reasons (Lloyd, 1988; Schrader, 1991) the combined use of taurine with homotaurine or with methionine should result in mutually potentiating effects. The simultaneous use of small amounts of purinergic compounds (not enough to produce significant hypotension) and taurine alone or taurine+homotaurine and/or with methionine are likewise supplementary and are expected to further potentiate mutually their analgesic and/or anesthetic, and protective effects.

Thus, according to one aspect of the present invention, there is provided a method of inducing analgesia or anesthesia in a mammal including the human, the method comprising administering to the mammal a therapeutically effective amount for inducing the analgesia or anesthesia of at least one agent selected from the group consisting of taurine, homotaurine and methionine.

In the foregoing, the agent may be administered alone as an analgesic or anesthetic formulation, or in combination as an anesthetic coadjuvant supplementing another anesthetic agent.

According to another aspect of the invention, there is provided a method of treating or preventing ischemic injury of tissues in general, but especially of the central nervous system, in a mammal including the human, the method comprising administering to the mammal a therapeutically effective amount for treating or preventing the ischemic injury of at least one agent selected from the group consisting of taurine, homotaurine and methionine. According to yet another aspect of the invention, there is provided a pharmaceutical formulation for inducing analgesia or anesthesia in a mammal including the human, comprising a therapeutically effective amount for inducing the analgesia or anesthesia of at least one agent selected from the group consisting of taurine, homotaurine and methionine. This formulation may consist essentially of one agent alone as an analgesic or anesthetic formulation or may comprise another supplementing anesthetic coadjuvant.

According to a further aspect of the invention, there is provided a pharmaceutical formulation for treating or preventing ischemic injury of tissues in general in a mammal including the human, comprising a therapeutically effective amount for treating or preventing the ischemic injury of at least one agent selected from the group consisting of taurine, homotaurine and methionine, either alone or may comprise another supplementing agent (generally an anesthetic or anticovulsant).

DETAILED DESCRIPTION OF THE INVENTION

In accordance with the present invention, a therapeutically effective amount of primarily exogenous taurine, and secondarily homotaurine and/or methionine are administered to a mammal including the human to mimic the keenly sought beneficial effects of adenosinergic approaches without the undesirable cardiovascular side-effects. In fact, in a number of pilot experiments in non-ischemic rabbits, the administration of the racemic mixture of exogenous taurine or methionine, either one separately or combined, resulted in profound electroencephalographic (EEG) changes, in a dose-dependent manner with practically no effects on blood pressure, indicative of deepening of the anesthetic level and functional quiescence of the brain. Anesthesia levels, from light to deep, have been well characterized by EEG changes (Faulconer A., 1960;Michenfelder J. D., (b)1988) from stage I (rapid but regular activity), II and III (slow, regular or irregular activity), IV (short lasting burst suppression), V (burst suppression of longer duration), to VI (no activity or flat EEG). Furthermore the EEG changes (burst suppression and/or left and downward shift of the power spectrum of the EEG activity) indicative of deep levels of anesthesia and depressed CNS function had profound correlation with brain cortical interstitial fluid levels of taurine which were related logarithmically to the dose of taurine given intravenously thus providing a non-invasive tool for monitoring the desired effects and required dosages to obtain specific functional changes without having to resort to actual tissue or interstitial fluid concentration determinations during inhibitory-taurinergic therapy (therapy aimed at modifying the brain tissue levels of taurine by administration of exogenous taurine, homotaurine or methionine, or other types of therapy directed to changing the levels of endogenous taurine and/or other inhibitory aminoacids such as glycine, which seems to be influenced by taurine). Hence the practical applicability of using taurine, homotaurine or methionine alone or in various combination(s) as analgesic/anesthetic agent(s) or as anesthetic coadjuvant(s) when supplemented to other anesthetic agents, or as analgesics that could be used in lieu of the widely used narcotics for the management of pain, without having the disadvantages of narcotics, i.e., respiratory depression. The addition of small amounts of purines (not enough to produce hypotension) will logically have mutually potentiating effects.

Obviously, taurine, homotaurine and/or methionine should be administered in sufficient quantities, either in a repetitive intravenous (IV) boluses or a continuous infusion, for as long a period the analgesic (or anesthetic) effect is desired, which may vary from a few hours, such as in postoperative pain management, to more extended periods (days or weeks) in the management of intractable pain in oncological patients for example. A loading dose of 1.0 to 2.0 mmol/kg of body weight followed by either a continuous drip or a periodic maintenance boluses is recommended.

The issue of when and for how long taurine, homotaurine and/or methionine ought to be given for tissue protection, will depend on the severity of the ischemia producing cause and the feasibility of specifically eliminating the cause of ischemia itself, but it (they) must be made available to the target tissue as early as possible. Ideally it (they) should be started before or shortly after the initiation of the ischemia and continued preferably beyond the time normal or close to normal blood flow is restored, since many of the injurious events occur at the time blood flow is restored, i.e., reperfusion to the already $Ca^{++}$ loaded ischemic tissue. Taurine, homotaurine and/or methionine, by preventing further $Ca^{++}$ loading and oxidation of lipids should minimize not only events occurring during ischemia but also many of such reperfusion events. A loading IV dose of taurine (alone or combined with homotaurine and/or methionine) with 2.0–3.0 mmol/kg of body weight (enough to obtain a functionally quiet CNS by EEG criteria) followed by a maintenance continuous IV drip or periodic IV boluses are recommended.

Since these beneficial effects are not limited to the CNS but are effects observable in other tissues as well, the indications for protective effects can be extended to many target organs, either in situ such as for resuscitation, or during cardiac, liver, renal or pancreatic surgery or in explanted organs such as for harvesting and preserving of donor organs for transplantation, for which perfusion solutions containing at least 1 or 2 mmol/l or more, are recommended.

When taurine is combined to methionine for protection, particularly of the CNS, the dosage for both agents may need adjustments since they are both supplementary and mutually potentiating, for which the EEG will be useful in guiding the therapy. Although the racemic mixture of methionine at the dose of 0.5 mmol/kg was used in our experiment, since it is believed that the L-isomer is the biologically active stereoisomer, particularly in the CNS, when using L-methionine, its dose must be adjusted accordingly. The same may be applicable to taurine or homotaurine.

In regards to method of delivery, the parenteral intravenous route is the preferred route, given as an initial loading bolus and then either repeated periodically or preferably as a continuous drip using any of the commonly available delivery devices, but other routes are not excluded such as intra-arterial, peritoneal, subcutaneous, intrathecal or even enteral. Whatever the method, it is necessary to attain interstitial concentrations of taurine sufficient to obtain a quiescent EEG and to maintain these concentrations of taurine in the brain extracellular fluid for an extended period of time, preferably over 8 hours, and still more preferably greater than the length thought to be under the danger of excitotoxicity, which might be 48 to 72 hours.

The inventors have proven in preliminary experiments that exogenously administered taurine alone mimics many, if not all the effects sought with purinergic compounds in the CNS or elsewhere, and hence the potential use of taurine, either alone or in combination with methionine or small amounts of purinergic compounds as therapeutic agent(s) in a/or for a wide variety of conditions (anesthetic, neurologic and non-neurologic such as cardiac protection in patients suffering from myocardial ischemic episodes or infarction or during heart surgery, or for donor organ preservation in transplantation of various organs), oriented to protect the organ from the potentially devastating effects of ischemia.

Taurine, homotaurine and methionine are naturally present aminoacids in practically every tissue. The natural metabolic pathways include conversion of homotaurine to taurine, and use of methionine for the endogenous production of adenosine (consequently ATP) and homo-cysteine (a precursor of taurine) (Huxtable, 1980; Lloyd, 1988;

Schrader, 1991). Taurine is especially well known to be used normally as a detoxifying substrate by the liver. Although toxicological studies have not been made, it is most likely that taurine, homotaurine and methionine are devoid of toxic effects when used at the therapeutically useful dosages or at least will have wide margins of safety which is a highly desirable feature for any substance to be used as a therapeutic agent.

Because, in various ischemic models, the required amounts of purinergic compounds to get only the desirable inhibition of the release of EAAs are reportedly to be small, on one hand, and the beneficial effects of taurine are dose dependent on the other, the combination of small amounts of the former and whatever is necessary of the latter is rational, and might avoid having to use large amounts of purinergic compounds that would have to be used if all the sought effects were to be obtained with purinergic compounds only with the consequent undesirable and unavoidable cardiovascular (hypotensive) effects. Furthermore the combined use with methionine, in inducing anesthesia and particularly for protection, is metabolically supplementary, not only to increase interstitial levels of adenosine and taurine by increasing their endogenous production (Huxtable, 1980; Lloyd, 1988; Schrader, 1991), but also to promote sparing of the endogenous ATP which is characteristically depleted during ischemic conditions, effect that would supplement the ultimately sought protective actions of the exogenous taurine or adenosinergic approaches.

Potential combinations of taurine, homotaurine or methionine may contain a number of other already available drugs including but not limited to adenine necleosides (adenosine or adenosine analogues) and nucleotides (ATP or ATP analogues), mannitol, vitamin C, glutathione, vitamin E and related compounds, magnesium, dantrolene, corticosteroids, promazine and related compounds, nicholin, 21-amino steroids, non-steroidal anti-inflammatory agents, other anti-inflammatory agents, calcium antagonists (nifedipine, diltiazim, nicardipine, etc), openers of $K_{ATP}$ channels in general with representatives such as pinacidil, nicorandil, chromakalim, among others, or other protective drugs that are in various phases of development or are to be developed in the future] or physical means such as hypothermia to mutually potentiate their protective effect.

Another aspect of the present invention is a method for improving blood circulation locally in a mammal. This method includes the steps of topically applying to a skin or mucosal area of the mammal a hypertonic solution of at least one compound selected from the group consisting of taurine and 1-methionine. The hypertonic solution preferably contains at least 5% by weight of taurine, and more preferably, the solution contains 7–10% by weight of taurine. The hypertonic solution may be a liquid or an ointment.

EXAMPLE 1

Figure 1:
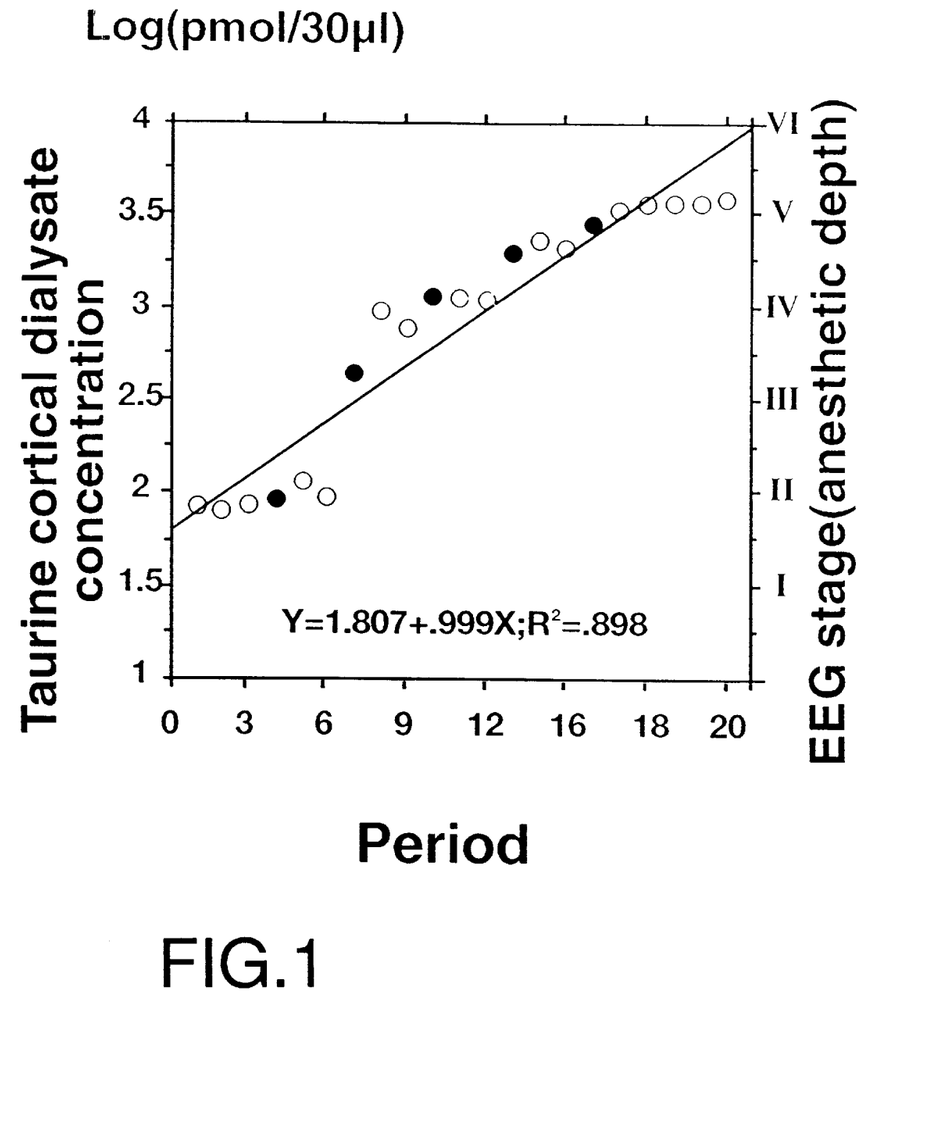
FIG. 1 is a graph showing brain cortical interstitial fluid levels of taurine which are related logarithmically to the dose of taurine given intravenously.

Dose-response of occipital cortical taurine concentration levels were measured by micro-dialysis technique, and EEG (frontal leads) were observed in a non-ischemic rabbit. The exogenously administered intravenous bolus of methionine (0.5 mmol/kg) induced tendency, though minimal, of elevation of the endogenous taurine levels, but produced typical and unequivocal EEG changes characterized by wide amplitude, relatively slow waves that are characteristic of stage II-III of EEG depth of anesthesia (Table 1, periods 4–6, FIG. 2), as compared to that of basal anesthesia condition (Table 1, periods 1–3, FIG. 2; EEG stage I, obtained with isoflurane 1.5% and mixture of $N_2O/O_2$ at 65:30%) prior to the administration of taurine. Incremental doses (intravenous bolus) of taurine (0.5 mmol/kg every 3 cortical interstitial fluid-dialysate collection periods of 22 minutes each period) starting at 0.5 mmol/kg, without changing other anesthetic conditions, resulted in EEG evidence of further deepening of the anesthesia level (periods 7–18, FIGS. 1 and 3–6), which can be summarized by the left and downward shift of the EEG spectrum (FIGS. 3–6) expressed in terms of Fourier transform power spectrum (FFT of one minute epochs of EEG taken at the end of each collection period). These EEG changes paralleled the logarithmic increases of the interstitial taurine cortical concentrations reflected in the dialysate taurine contents (Table 1, FIG. 1), and for example after the dose of 2.0 mmol/kg of taurine (periods 16–21) the EEG reached stage IV-V (burst suppression) consistent and persistently.

TABLE 1

Dose-Response

Figure 2:
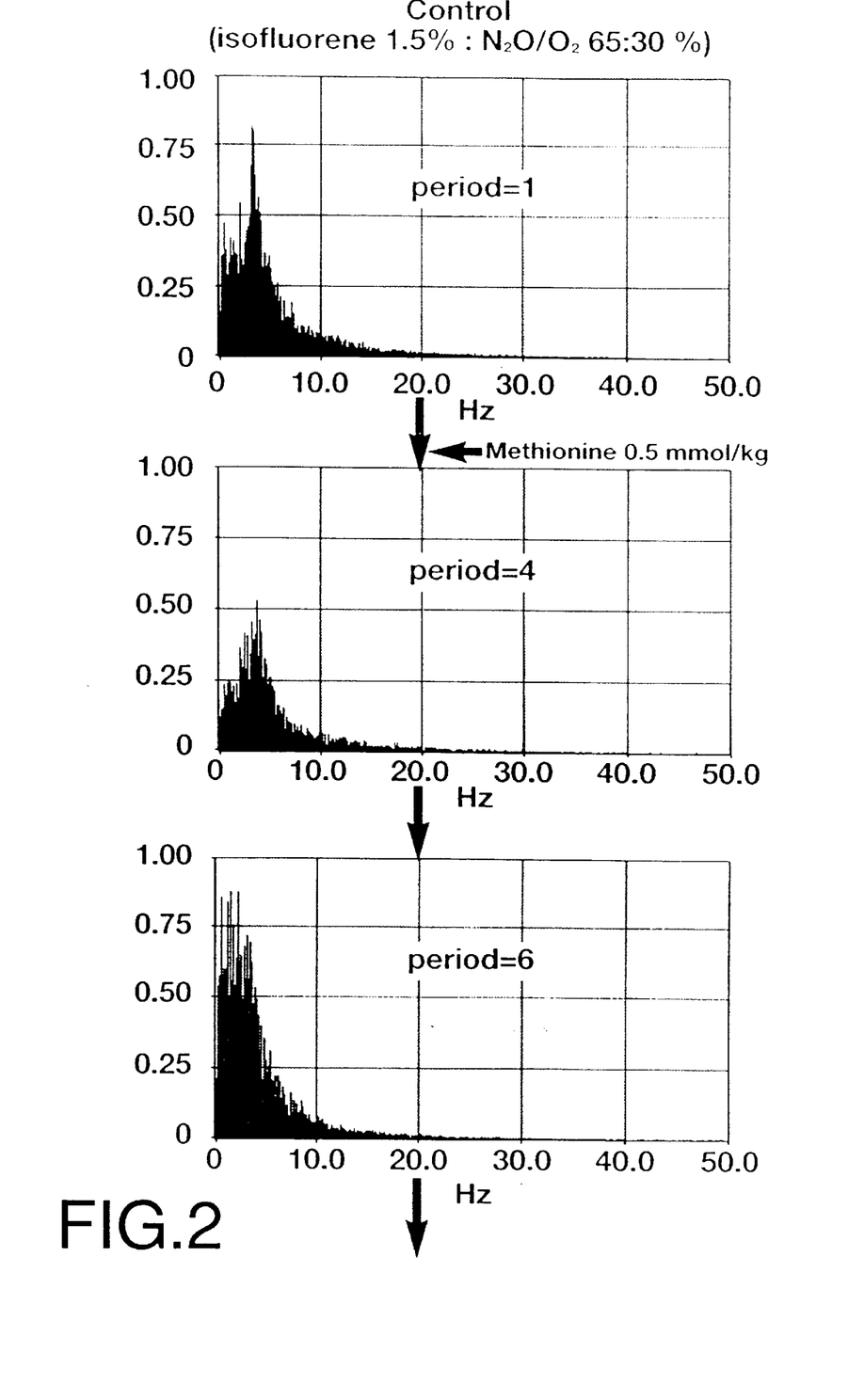
FIGS. 2 to 6 are illustrations of the power spectrum of the electroencephalogram (EEG) in a non-ischemic rabbit obtained during the administration of methionine or incremental amounts of taurine.
Figure 3:
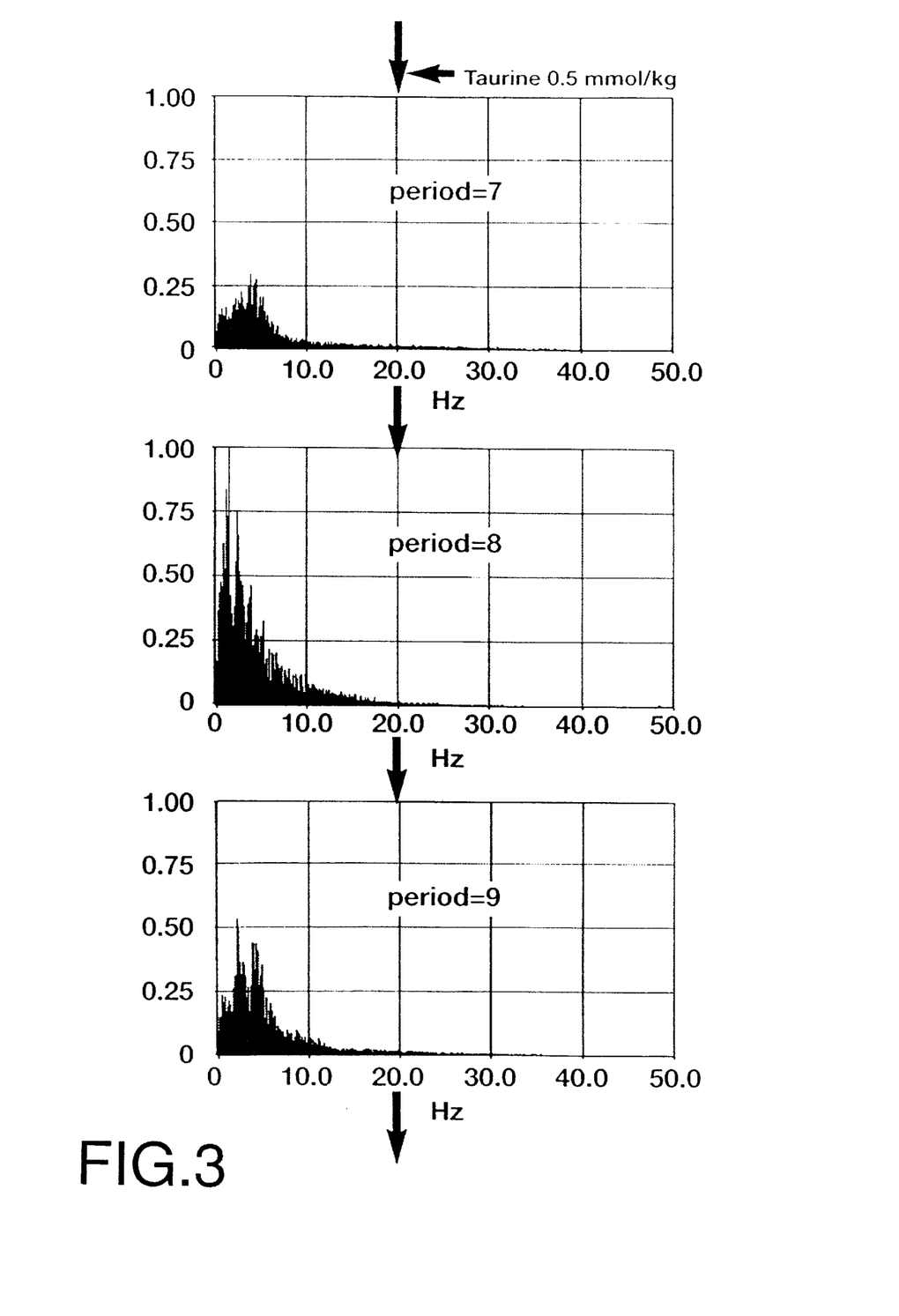
Figure 4:
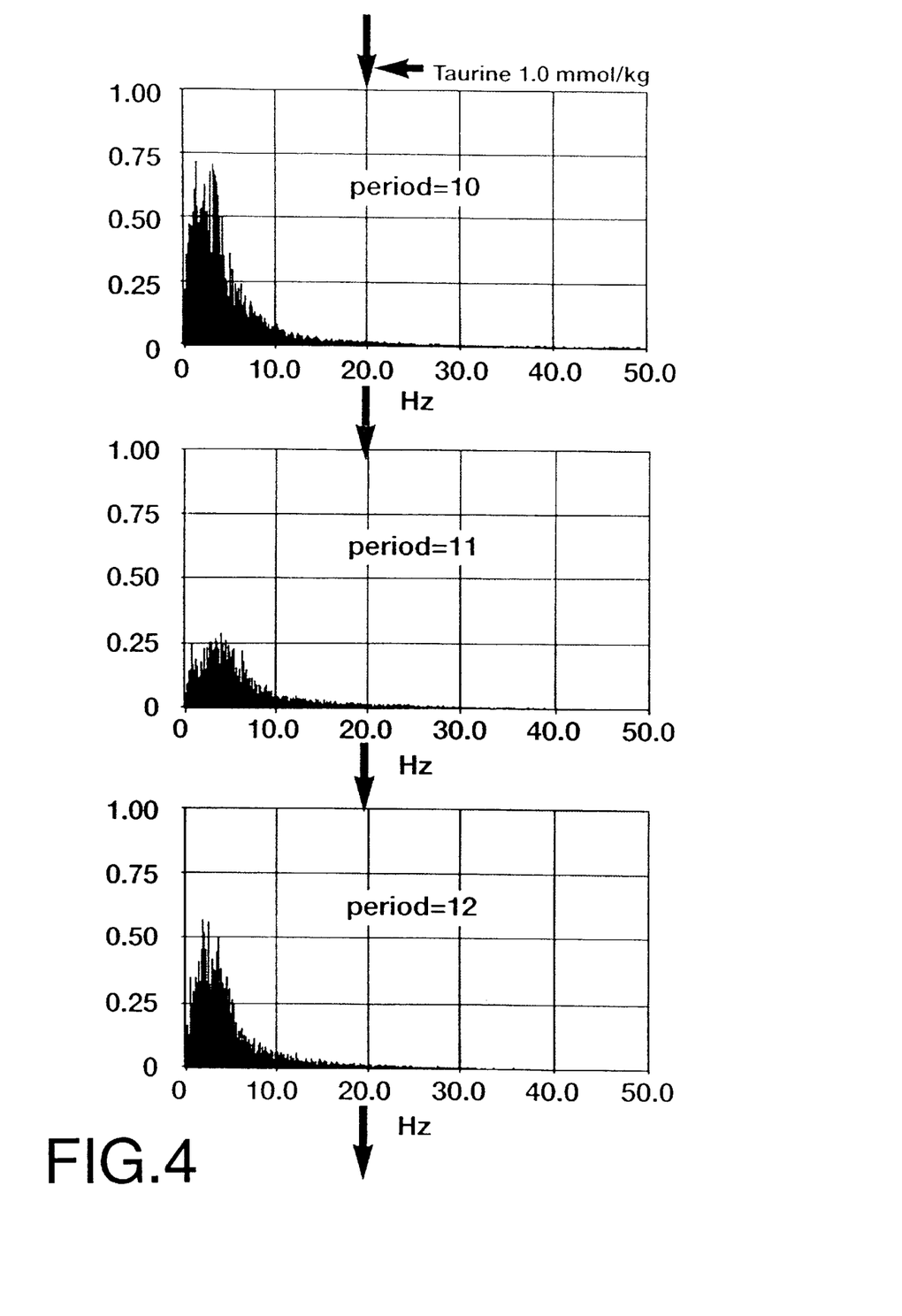
Figure 5:
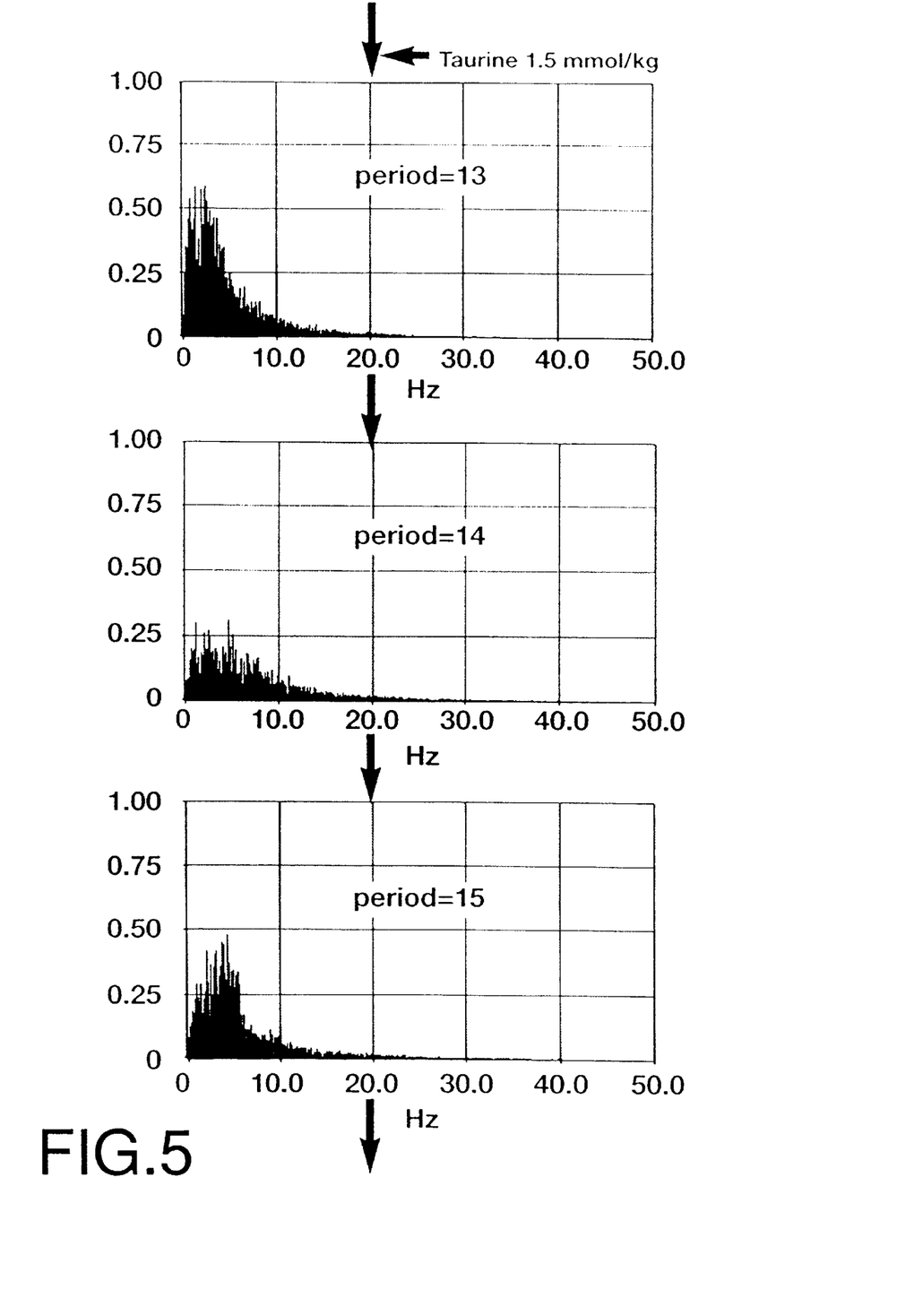
Figure 6:
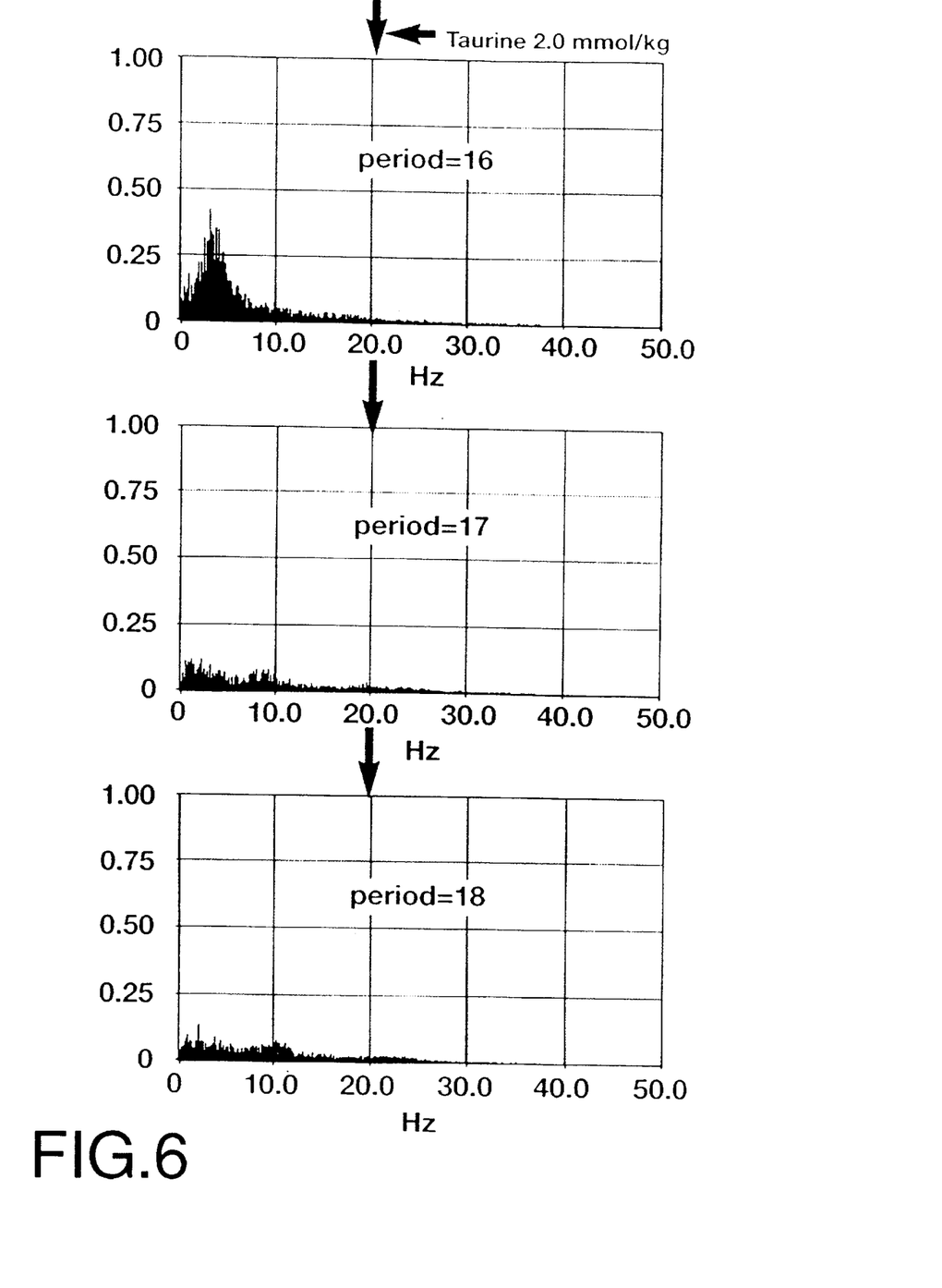

| | | Cortical Concentration (pmol/30 μL Dialysate) | | EEG | |
|---|---|---|---|---|---|
| Sample No. | | pmol | Log | EEG Stage I-VI | FFT Power Spectrum |
| Control | 1 | 87.8 | 1.9435 | I | FIG. 2 |
| | 2 | 82 | 1.9138 | I | |
| | 3 | 87.8 | 1.9435 | I | |
| M:0.5 mmol/kg ●| 4 | 94.8 | 1.9768 | II | FIG. 2 |
| | 5 | 118 | 2.0719 | III | |
| | 6 | 96 | 1.9823 | III | FIG. 2 |
| T:0.5 mmol/kg ●| 7 | 453 | 2.6551 | III | FIG. 3 |
| | 8 | 976 | 2.9894 | III | FIG. 3 |
| | 9 | 798 | 2.9021 | III–IV | FIG. 3 |
| T:1.0 mmol/kg ●| 10 | 1151 | 3.0607 | III–IV | FIG. 4 |
| | 11 | 1164 | 3.0645 | III–IV | FIG. 4 |
| | 12 | 1105 | 3.0414 | III–IV | FIG. 4 |
| T:1.5 mmol/kg ●| 13 | 1982 | 3.2967 | IV | FIG. 5 |
| | 14 | 2347 | 3.3711 | IV | FIG. 5 |
| | 15 | 2074 | 3.3161 | IV | FIG. 5 |
| T:2.0 mmol/kg ●| 16 | 2848 | 3.4548 | IV–V | FIG. 6 |
| | 17 | 3430 | 3.5353 | V | FIG. 6 |
| | 18 | 3628 | 3.5599 | V | FIG. 6 |

Methionine (M) or Taurine (T) was administered as an IV bolus over a 3 minute period at the beginning of the corresponding fraction period (●).
EEG = Electroencephalogram; FFT = Fourier transform or EEG power spectrum of one minute EEG epoch; EEG anesthesia stage I–VI (see text).

EXAMPLE 2

Figure 7:
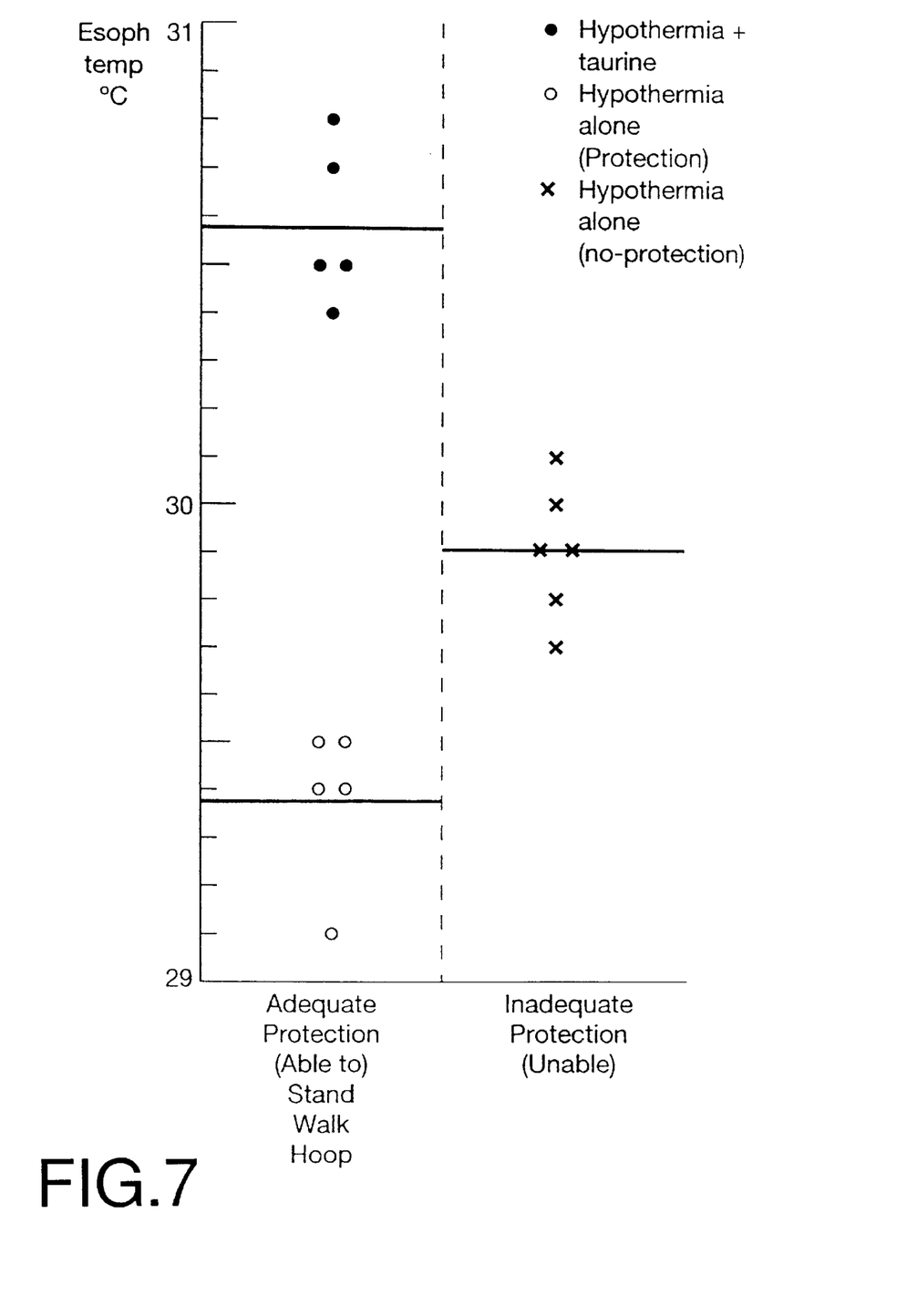
FIG. 7 is a graph showing the protective effect afforded by taurine in a spinal cord ischemia model in rabbits.

The protection afforded by taurine was examined in the well known spinal cord ischemia model in the rabbit (reversible clamping of the abdominal aorta below the renal artery) of one hour duration. The protective effects were compared against what golden standard of the protective methods: hypothermia, which is well characterized by the increasing protective efficacy, within a certain range, with the degree of hypothermia established at the time ischemia occurs. In one group of animals (○) sufficient degree of hypothermia (mean esophageal temperature of 29.38° C.) to obtain adequate protection (the rabbit would recover normal spinal cord function within 6 hours of establishing spinal cord reperfusion following one hour of ischemia) was determined; in another group (x) the degree of hypothermia induced was slightly less (esophageal temperature being 29.9° C. or 0.52° C. higher than the former group) so that animals would not recover cord function, and in a third group (●) 10 mmols/kg of body weight of taurine prepared as a 10% solution (by weight) was administrated: one third of it at the time of induction of anesthesia, one third during the induction of hypothermia (which turned out to be 30.58° C. or 1.2° C. higher than the first (○) group, and 0.68° C. higher than the second (x) group), and the remaining one third 5 minutes prior to establishing reperfusion of the spinal cord (declamping of the aorta). As depicted in the FIG. 7, animals receiving taurine were all adequately protected at temperatures that hypothermia alone failed to achieve, functional recovery being persistent 24 hours later, indicating that the spinal cord was indeed adequately protected during the one hour of blood perfusion deprivation, with no evidence of gross delayed untoward phenomena at least for 24 hours.

In addition, pilot experiments with isotonic taurine solution was found to be less effective than the 10% (hypertonic) solution of taurine. A hypertonic solution is a solution having an osmotic pressure greater than that of normal scrum or plasma (300 mosm/l) . The protective effects of taurine could further be potentiated with a number of other medications aimed to reduce the production of free radicals such as mannitol, deferoxamine and vitamin C, or to prevent the increase of intracellular Na or Ca such as Mg and dantrolene, or inhibitors of phospholipase C such as chlorpromazine and nicholin leading to the conclusion that when taurine is used with one or more other medication(s) with protective properties on their own, even through the protective effects might not be an algebraic summation of the activity of each one of the components the net resulting effect would be a greater protective efficacy than the individual component given separately (potentiation).

The therapeutically effective taurine doses for clinical use is 6–10 mmol/kg of body weight, when administered as a hypertonic solution. The concentration of taurine in the hypertonic solution is preferably at least 5% by weight. The more concentrated the better (to be able to give the same dosage of taurine in the least volume), but considering the physical properties of solubility of taurine (13% at room temperature of 23° C.) a 7% to 10% solution would probably be the most workable concentration, taking into account also the volume tolerance when given within a short period of time.

EXAMPLE 3

Since many substances with protective effects exert the protection by promoting blood flow to the affected area in addition to the specific mechanism by which exert the protective action, the blood flow effects of topical taurine solution to the dorsal aspect of the toes were examined by measuring skin temperature with an infra-red camera in a patient with frostbite of the left foot (4th toe), without and with iced cold water immersion challenge for 5 seconds. The skin temperature reflects the blood flow to the area, the warmer the greater blood flow.

How fast the skin temperature returns to normal after a short period of immersion into iced-water is a commonly used clinical test to evaluate the blood flow to the area and its neurogenic control. The non-specific protective vasodilating effect exerted by the topically absorbed taurine will be manifested as increase of temperature, over the basal temperature or by accelerating the recovery of the basal temperature after iced-water immersion.

Accordingly as can be seen on the tables 2 and 3, topical taurine increases the temperature of the toes where it was applied, whether it is applied without or with prior challenge of exposure to cold. The maximal effects are seen between 15 to 20 minutes after its topical application in both situations. Previous studies of spinal cord ischemia have shown the most protective effects of hypertonic solutions as compared to isotonic or hypotonic solutions, and similar correlation is predicted for the vascular effects, though only a 10% solution was tested.

Although of slightly lesser magnitude and not tabulated, similar response is observed when applied to normal subjects, not only on feet, but also on hands and the forehead. The implication being that it should be especially effective when applied to patients who have various degrees of neurovascular disorders. Homotaurine or methionine can be used in place of taurine to obtain the same effect as that of taurine. However, taurine can offer the most remarkable effect.

TABLE 2

No Iced Water Challenge

Toe-Skin Temperature

| Room Temp.: 27.5° C. | Evaluation-Side Average 4* Toes (1,2, 4, 5)* | % of Max Change | 3rd | Contra-Lateral Side Average 4* Toes (1, 2, 4, 5)* | 3rd |
|---|---|---|---|---|---|
| Baseline | 32.25° C. | — | 31.4° C. | 31.85° C. | 31.5° C. |
| 0 min | Topical Taurine | — | Nothing | Topical Water | Nothing |
| 5 mins | 33.02° C. | 81.05% | 32° C. | 31.67° C. | 31.9° C. |
| 10 mins | 32.7° C. | 47.37% | 31.8° C. | 31.2° C. | 31.1° C. |
| 15 mins | 32.9° C. | 68.4% | 32.3° C. | 31.37° C. | 31.8° C. |
| 20 mins | 33.2° C. | 100% | 32.1° C. | 31.85° C. | 31.7° C. |
| 25 mins | 33.02° C. | 81.05% | 32.1° C. | 31.37° C. | 31.7° C. |
| 30 mins | 32.87° C. | 65.26% | 31.9° C. | 31.6° C. | 31.9° C. |

TABLE 3

Iced Water Challenge

Toe Skin Temperature

| Room Temp.: 27.7° C. | Average 5 Toes Evaluation Side | % Recovery | Average 5 Toes Contra-Lateral Side | % Recovery |
|---|---|---|---|---|
| Baseline | 32.62° C. | — | 31.92° C. | — |
| Iced Water (5 seconds) | 24.2° C. | — | 21.56° C. | — |
| 0 min | Topical Taurine | — | Topical Water | — |
| 5 mins | 29.38° C. | 61.52% | 26.58° C. | 48.65% |
| 10 mins | 31.42° C. | 85.75% | 28.16° C. | 63.71% |
| 15 mins | 31.66° C. | 88.6% | 28.6° C. | 67.95% |
| 20 mins | 30.92° C. | 79.81% | 28.06° C. | 62.74% |
| 25 mins | 31.5° C. | 86.7% | 28.16° C. | 63.71% |
| 30 mins | 31.04° C. | 79.81% | 27.46° C. | 56.95% |

EXAMPLE 4

The protection afforded by hypertonic (10% aqueous solution) taurine was examined with the well-known spinal cord ischemia model in the rabbit (reversible clamping of the abdominal aorta below the renal artery) of one-hour duration.

The standard of the protective methods, hypothermia (temperature lower than the normal temperature of 38° C. to 39° C. in mammals), was used to assess and compare the protective effects of hypertonic taurine. Hypothermia was induced by placing iced water bags on the abdomens as well as on the anterior aspect of the chests of anesthetized rabbits, while the esophageal temperature was continuously monitored with a thermistor temperature probe. The iced water bags were removed when a particular desired temperature was reached, allowing for the after-drop (1.5° C. to 1.8° C.) that occurs after removing the bags. When the esophageal temperature reached the target temperature, the infra-renal abdominal aorta was temporarily clamped (a well known spinal cord ischemia model in rabbits) for one hour.

To quantify the degree of protection, the neurologic spinal cord function recovery was assessed by a scoring method (from 0 =anesthesia, to 6=full recovery; as explained later) with measurements taken every 15 minutes after anesthesia wash out, allowing a 90-minute period of re-warming after reperfusion or declamping of the infra-renal abdominal aorta. Although the first 90 minutes after anesthesia wash out reflects mostly the time required to recover from the effects of anesthesia, the repair of the damage inflicted by the ischemic (decreased blood flow) period starts as soon as the blood flow is re-established (re-perfusion).

First, the pure hypothermic temperature required to protect the ischemic spinal cord for one hour was determined. It was found necessary to cool the rabbit down to 29.4±0.07° C. to protect the animals from one hour of ischemia. Animals cooled to only 29.9±0.05° C. failed to recover, but when 10 mmols/kg of taurine as a 10% solution was administered during the cooling phase, all animals recovered fully even if the hypothermia was only down to 30.4±0.07° C. The same amount of taurine, but given as an iso-tonic (3.75%) solution, in animals cooled to 30.3±0.05° C. failed to protect them.

[Objective neurologic scoring (NS) system]

Rabbits are observed restrained by a stationary collar in a special temperature controlled cage, equipped with means to provide respiratory care (end expiratory oxygen and carbon dioxide monitoring, mechanical ventilation, positive end-expiratory pressure or oxygen enriched air as required, usually the first 60–90 minutes following anesthesia wash-out) as well as graded interchangeable hurdles (3.5 cm and 6.5 cm high) to be placed under the abdomen (hip portion). Each recovery stage is defined by the objectively measurable ability of the rabbit to clear the specific height hurdle and not by the observer's subjective evaluation as follows:

0: Still under the effects of anesthesia.

1: Assessed in a) supine position: responsive to stimuli; moves ears and/or head. Front limbs movements present, but unable to move hind limbs; might be able to flex pelvis and abdomen over the chest spontaneously or in response to any stimuli, by contraction of abdominal muscles, but not the hind limbs proper, or b) Prone position: able to sustain the head erect but hind limbs are either flaccid or spastic in extension and unable to arch the trunk. Tail movements might be present.

2: Vigorous extension of hind limbs (to the point of being able to arch the trunk) might be present but unable to retract (flex) them under the abdomen when placed prone with the hind limbs extended on flat surface in the cage.

3: Capable of retracting (flexing) hind limbs on both sides under the abdomen if hind Limbs are extended on a flat even surface, either spontaneously or in response to painful tail pinching. One half point credit for each hind limb.

4: Capable of retracting (flexing) both hind limbs extended over a hurdle 3.5 cm high, either spontaneously or in response to painful tail pinching. The back is still straightened and unable to take the normal (rounded back) posture. Falls to one side unless supported.

5: Vigorous retraction (flexion) of both hind limbs in, response to painful tail pinching over a 6.5 cm high hurdle. The back is still straight and unable to keep the normal (rounded back) posture, although may be capable of repositioning the body to walk. Lateral support no longer needed.

6: Vigorous retraction (flexion) of both hind limbs over a 6.5 cm high hurdle spontaneously. Able to maintain the normal (rounded back) posture, capable of repositioning the body to walk, capable of kicking, capable of hopping when neck restrain is removed.

TABLE 4

| Elapsed Time | | Degree of Spinal Cord Function Recovery (NS 0–6) | | | | | | |
|---|---|---|---|---|---|---|---|---|
| | | Group 1: Hypothermia + Taurine (10 mmol/kg) | | | | Group 2: Hypothermia alone | | |
| Re-perfusion | Anesthesia Wash-out | A(10%; n = 5) | | B(3.75%; n = 6) | | b(30° C.; n = 6) | | a(29.5° C.; n = 6) |
| (minutes) | | Mean | SD | Mean | SD | Mean | SD | Mean | SD |
| 90 | 0 | 0 | 0 | 0 | 0 | 0 | 0 | 0 | 0 |
| 150 | 60 | 3 | 1.41 | 0.8 | 0.4 | 1 | 0.58 | 2.2 | 0.98 |
| 210 | 120 | 4.4 | 0.8 | 1.3 | 0.5 | 2.5 | 1.6 | 5 | 0.6 |
| 270 | 180 | 5.8 | 0.4 | 1.17 | 0.37 | 2.83 | 1.67 | 5.8 | 0.4 |
| 330 | 240 | 6 | 0 | 1.17 | 0.37 | 2.83 | 1.67 | 6 | 0 |
| 360 | 270 | 6 | 0 | 1.667 | 1.491 | 2.83 | 1.67 | 6 | 0 |

Group 1: Hypothermia (not enough to be protective by itself=30.5° C.)+Taurine (10mmol/kg intravenously given before ischemia)

Group 1A: Taurine administrated as 10% hyperosmotic solution.

Group 1B: Taurine administrated as 3.75% isoosmotic solution

Group 2: Hypothermia alone

Group 2a: Cold enough for hypothermia to be protective by itself

Group 2b: 0.5° C. higher temperature than 2a but colder than Group 1.

NS (neurologic score): 0 (=Anesthesia) to 6 (=full recovery)

SD=Standard deviation

To further assess protective effects, the rate of recovery was used as an indicator of the efficacy of the protective strategy. The sooner a score of 6 is reached, the better the protection. As summarized in Table 4, animals receiving 10% taurine recover function faster (higher scores earlier) than equally protected (when judged 6 hours after reperfusion) by hypothermia alone, although the hypothermia alone group has a faster early recovery. This delay of the taurine receiving group, is delay in waking-up and reflects the anesthetic effects of taurine.

Animals that had recovered by 6 hours remained recovered the next day; those with a score of <5 did not improve any further, if any had worsening of the score the next day. Thus when the protection is adequate, full recovery can be anticipated within 6 hours of reestablishment of blood flow (re-perfusion) and delayed phenomena should not occur.

None of the animals receiving the same amount of taurine but in isotonic solution recovered function, thus emphasizing the importance of being a hypertonic solution.

Administration of iso-osmolar concentration of taurine would have been the logical application of prior art teachings based on the anti-calcic effects, and following the basic pharmacological principles of administering drugs in iso-osmolar concentrations. However it is obvious that for taurine to be protective in a predictable manner, it must be hyper-osmolar. Our contention is that the hypertonic solution prevents the cytotoxic intracellular edema from developing, which the iso-osmolar solution fails to do.

Since taurine solubility is reported to be 13% at 25° C., 10% was chosen for logistic reasons, but in theory the more concentrated a given amount of taurine solution, the greater the anti-edema effect should be. Although the amount chosen of 10 mmol/kg was effective to protect the ischemic period of one hour when combined to hypothermia of 30.5° C., the ideal timing and dosage might be different for different ischemic periods and for different temperatures.

The protective effects of taurine could further be enhanced in pilot studies with mannitol, deferoxamine, nicholin and vitamin C, and in theory with a number of other medications aimed to reduce the production of free radicals or to prevent the increase of intracellular Na or Ca (Mg and dantrolene), or inhibitors of phospholipase C (chlorpromazine) leading to the conclusion that when taurine is used with one or more other medication(s) with protective properties on their own, even though the protective effects might not be an algebraic summation of the activity of each one of the components, the net resulting effect would be a greater protective efficacy than the individual component given separately (enhancement or potentiation).

Based on these results, the following arguments can be derived:

I) The therapeutically effective taurine doses for clinical use is 6 to 10 mmol/kg of body weight when it is administered as a hypertonic solution.

II) The concentration of taurine in preferably at least 5% by weight. The more concentrated the better (to be able to give the same dosage of taurine in the least volume), but considering the physical properties of solubility of taurine (13% at room temperature of 25° C.), a 7% to 10% solution would probably be the most workable concentration, taking into account also the volume tolerance by the patient when given over a short period of time.

III) Potential combinations of taurine, homotaurine or methionine to varying amounts of a number of other already-available drugs or physical means such as hypothermia to mutually potentiate their protective effect. Other already-available drugs included but are not limited to, adenine necleosides (adenosine or adenosine analogues) and nucleotides (ATP or ATP analogues), mannitol, vitamin C, glutathione, vitamin E and related compounds, magnesium, dantrolene, corticosteroids, promazine and related compounds, nicholin, 21-amino steroids, non-steroidal anti-inflammatory agents, other anti-inflammatory agents, calcium antagonists (nifedipine, diltiazim, nicardipine, etc), openers of KATP channels in general with representatives such as pinacidil, nicorandil or chromakalim among others, or other protective drugs that are in various phases of development.

EXAMPLE 5

The therapeutic use of taurine, d or l or dl-methionine, homo-taurine, either alone or in combination to induce vasodilatation in general, but particularly in the perioperative period (before, during and after an operative procedure) without producing excessive hypotension nor cardiac depression is further examined.

Vasodilatation effects can be assessed by measuring the blood pressure with a fluid-filled intra arterial catheter attached to a pressure transducer. The blood pressure is the resultant of the interaction of the resistance to the blood flow offered by the vascular tree (determined by the degree of vaso-dilatation) on one hand and the amount of blood ejected by each cardiac contraction (cardiac output). The ideal vaso dilator drug is one that selectively decreases the vascular resistance without affecting the cardiac output. i.e. without producing cardiac depression. As part of the normal reflex function, heart rate increases (tachycardia) as the blood pressure is decreased regardless of the etiology, whether caused by the effects of a vasodilator or blood loss. However in clinical practice, especially in the perioperative period, tachycardia is not a desirable effect, and other drug(s) to decrease the heart rate, which is(are) cardiac depressive in general, is(are) often concomitantly used.

Tables 5A–5C summarize the blood pressure response recorded every 30 seconds following a bolus of either 3.3 mmol/kg of taurine (10% or 3.75% concentration) or of 1 to 1.75 mmol/kg of l-methionine given intravenously every 3 minutes for a total of 3 boluses. Because the depth of anesthesia and amount of fluid administered for the different experiments were not uniform since they had been enrolled to different studies, the results are not directly comparable, but the vaso-dilatory effect is evident; the magnitude of the vasodilating response, whether given as a hypertonic (10%) or isotonic (3.75%) solution of taurine is similar. The response is apparent as early as 30 seconds after the first dose but is persistent and consistent 3 minutes after the first bolus and following the second bolus. The heart rate decrease (bradychardia) is attained without depressing the cardiac function (cardiac output), being a characteristic and highly desirable effect. Though not tabulated, the cardiac function was estimated by the end-expiratory carbon dioxide concentrations which remained unaffected or if any increased in an animal ventilated at the same rate as that required to obtain an end-expiratory carbon dioxide of 5.0% at the basal condition, indicating unchanged or increased cardiac output.

TABLE 5

| | Pre | After First Bolus (seconds) | | | | | | After Second Bolus (seconds) | | | | | | After Third Bolus (seconds) | | | | | |
|---|---|---|---|---|---|---|---|---|---|---|---|---|---|---|---|---|---|---|---|
| | | 30 | 60 | 90 | 120 | 150 | 180 | 30 | 60 | 90 | 120 | 150 | 180 | 30 | 60 | 90 | 120 | 150 | 180 |
| Hyper-Osmotic Taurine (10%); Bolus (3.3 mmol/kg) every 3 minutes; n = 12 | | | | | | | | | | | | | | | | | | | | |
| Systolic Blood Pressure (mmHg) | | | | | | | | | | | | | | | | | | | | |
| Mean | 125 | 119 | 118 | 117 | 117 | 116 | 118 | 115 | 116 | 114 | 112 | 111 | 109 | 110 | 109 | 107 | 105 | 103 | 101 |
| SD | 15.3 | 14.9 | 15.2 | 15.7 | 15.7 | 16.1 | 16.3 | 19.5 | 21.6 | 21.7 | 22.5 | 23.4 | 23.9 | 21.5 | 22.7 | 22.4 | 22.5 | 20.9 | 19.9 |

TABLE 5-continued

|  | Pre | After First Bolus (seconds) | | | | | | After Second Bolus (seconds) | | | | | | After Third Bolus (seconds) | | | | | |
|---|---|---|---|---|---|---|---|---|---|---|---|---|---|---|---|---|---|---|---|
|  |  | 30 | 60 | 90 | 120 | 150 | 180 | 30 | 60 | 90 | 120 | 150 | 180 | 30 | 60 | 90 | 120 | 150 | 180 |
| Diastolic Blood Pressure (mmHg) | | | | | | | | | | | | | | | | | | | |
| Mean | 65.8 | 47.9 | 49.8 | 49.5 | 49.5 | 49.3 | 52.7 | 45.9 | 47.7 | 45.8 | 45 | 44.5 | 44.5 | 40.5 | 40.7 | 40.1 | 38.9 | 37.3 | 36.6 |
| SD | 23.9 | 17.3 | 16.7 | 17 | 19 | 19.1 | 20.4 | 22.7 | 24.4 | 23.9 | 23.8 | 24.6 | 26.8 | 25.1 | 23.8 | 23.5 | 22.3 | 21 | 20.5 |
| Differential (mmHg) | | | | | | | | | | | | | | | | | | | |
| Mean | 59.4 | 71.1 | 68.2 | 67.4 | 67.5 | 67 | 65 | 69.5 | 67.8 | 68.1 | 66.8 | 66.1 | 64.9 | 69.8 | 67.9 | 67.3 | 66 | 66.2 | 64.2 |
| SD | 21.6 | 22.1 | 22 | 22 | 21.7 | 21.8 | 20.6 | 21.9 | 21.3 | 21.5 | 21 | 21.6 | 21.9 | 23.3 | 22.7 | 22.6 | 22.7 | 20.6 | 20.4 |
| Mean Blood pressure (mmHg) | | | | | | | | | | | | | | | | | | | |
| Mean | 86.8 | 71.6 | 72.4 | 71 | 72 | 71.5 | 74.4 | 69.3 | 70.3 | 68.4 | 67.3 | 66.4 | 66.2 | 63.8 | 64.1 | 62.5 | 60.8 | 59.2 | 58 |
| SD | 20.4 | 12.8 | 12.7 | 13.6 | 14.8 | 15 | 16.5 | 19 | 21.3 | 20.8 | 21.2 | 22 | 23.8 | 21.4 | 19.5 | 20.4 | 19.7 | 18.6 | 17.9 |
| Heart Rate | | | | | | | | | | | | | | | | | | | |
| Mean | 288 | | | | 283 | | | | | | 270 | | | | | | 264 | | |
| SD | 30.3 | | | | 26.4 | | | | | | 31 | | | | | | 35.4 | | |
| Iso-Osmotic Taurine (3.75%); Bolus (3.3 mmol/kg) every 3 minutes; n = 6 | | | | | | | | | | | | | | | | | | | |
| Systolic Blood Pressure (mmHg) | | | | | | | | | | | | | | | | | | | |
| Mean | 153 | 137 | 134 | 129 | 124 | 121 | 118 | 98.3 | 96.3 | 95.3 | 94.8 | 94.5 | 95.2 | 101 | 101 | 103 | 104 | 105 | 106 |
| SD | 16.1 | 24.8 | 26.2 | 25.6 | 25.1 | 26 | 27 | 29.9 | 29.3 | 29.1 | 29.1 | 29.4 | 25.1 | 15.4 | 14.2 | 13.4 | 13.6 | 14.3 | 15.5 |
| Diastolic Blood Pressure (mmHg) | | | | | | | | | | | | | | | | | | | |
| Mean | 80.7 | 67.2 | 65.8 | 59.3 | 54 | 50.3 | 48.8 | 32.5 | 32.5 | 32.3 | 32.8 | 32 | 32.2 | 29.5 | 29.5 | 32.8 | 32.7 | 33.8 | 34.5 |
| SD | 21.8 | 22 | 19.9 | 15.4 | 12.6 | 10.4 | 10.3 | 9.8 | 10 | 10.1 | 11.1 | 12.5 | 12 | 9.7 | 9 | 10.6 | 11.3 | 12.2 | 11.9 |
| Differential (mmHg) | | | | | | | | | | | | | | | | | | | |
| Mean | 72.2 | 70.2 | 67.8 | 69.7 | 70.2 | 70.3 | 69.2 | 65.8 | 63.8 | 63 | 62 | 62.5 | 63 | 71.2 | 71.2 | 69.8 | 71.2 | 70.8 | 71.8 |
| SD | 14.6 | 17 | 16.2 | 17.6 | 18.6 | 20.5 | 20.2 | 25.8 | 27.2 | 27.1 | 26.7 | 26.9 | 22.9 | 16.4 | 15 | 14.5 | 15.2 | 15.1 | 15.1 |
| Mean Blood pressure (mmHg) | | | | | | | | | | | | | | | | | | | |
| Mean | 105 | 90.7 | 88.2 | 82.5 | 77.2 | 73.7 | 71.8 | 54.5 | 53.8 | 53.5 | 53.5 | 53 | 53.2 | 53.2 | 53.3 | 56 | 57 | 57.5 | 58.5 |
| SD | 18.7 | 21.6 | 20.7 | 17.5 | 15.4 | 14.3 | 14.9 | 14.5 | 13.9 | 13.7 | 14.5 | 15.2 | 13.5 | 9 | 8.6 | 9.4 | 9.8 | 10.7 | 11.3 |
| Heart Rate (mmHg) | | | | | | | | | | | | | | | | | | | |
| Mean | 307 | | | | 282 | | | | | | 260 | | | | | | 260 | | |
| SD | 15.9 | | | | 12.9 | | | | | | 24.5 | | | | | | 23.2 | | |
| Iso-Osmotic Methionine (4.5%); Bolus (1.0 or 1.75 mmol/kg) every 3 minutes; n = 3 | | | | | | | | | | | | | | | | | | | |
| Systolic Blood Pressure (mmHg) | | | | | | | | | | | | | | | | | | | |
| Mean | 130 | 122 | 122 | 120 | 117 | 115 | 121 | 122 | 121 | 119 | 114 | 111 | 110 | 109 | 110 | 108 | 104 | 104 | 106 |
| SD | 21.9 | 22.8 | 26.4 | 29.7 | 32.4 | 37 | 30.9 | 24.7 | 30.4 | 30.8 | 30.2 | 25 | 23.6 | 19.7 | 19.9 | 20.5 | 23.9 | 22.1 | 23 |
| Diastolic Blood Pressure (mmHg) | | | | | | | | | | | | | | | | | | | |
| Mean | 82.7 | 75 | 76 | 73.3 | 71.7 | 69.7 | 72.3 | 75.3 | 76.3 | 72.3 | 66.3 | 65.3 | 64.7 | 66 | 66 | 64.7 | 59.7 | 59.7 | 62.3 |
| SD | 30.3 | 23.6 | 28.1 | 29.3 | 31.8 | 33.9 | 28.3 | 23.4 | 27.9 | 28.1 | 27.7 | 23.8 | 20.2 | 16.3 | 17.7 | 17.9 | 21.5 | 21.5 | 17.8 |
| Differential (mmHg) | | | | | | | | | | | | | | | | | | | |
| Mean | 47.3 | 47 | 45.7 | 46.7 | 45.7 | 47 | 48.3 | 47 | 45 | 46.3 | 47.3 | 46 | 45 | 43.3 | 44 | 45.7 | 44 | 44.3 | 43.7 |
| SD | 14.7 | 4.08 | 3.86 | 4.19 | 2.62 | 4.24 | 4.64 | 4.24 | 3.27 | 4.64 | 5.25 | 4.97 | 4.55 | 4.11 | 4.24 | 1.89 | 10.2 | 10.8 | 8.99 |

TABLE 5-continued

| | Pre | After First Bolus (seconds) | | | | | | After Second Bolus (seconds) | | | | | | After Third Bolus (seconds) | | | | | |
|---|---|---|---|---|---|---|---|---|---|---|---|---|---|---|---|---|---|---|---|
| | | 30 | 60 | 90 | 120 | 150 | 180 | 30 | 60 | 90 | 120 | 150 | 180 | 30 | 60 | 90 | 120 | 150 | 180 |
| Mean Blood pressure (mmHg) | | | | | | | | | | | | | | | | | | | |
| Mean | 101 | 90.7 | 92 | 89 | 87 | 85 | 88.7 | 91.3 | 91.3 | 87.7 | 82 | 80.3 | 79.7 | 80.7 | 81 | 79.3 | 74.3 | 74.7 | 76.7 |
| SD | 29 | 23.5 | 27.3 | 29.3 | 32.1 | 34.9 | 29.2 | 23.8 | 28.5 | 29 | 28.2 | 24.2 | 21.5 | 17.2 | 184 | 189 | 21.8 | 21.1 | 19.3 |
| Heart Rate | | | | | | | | | | | | | | | | | | | |
| 1 (1.0 mmol/l) | — | | | | | | | — | | | | | | — | | | | | — |
| 2 (1.0 mmol/l) | — | | | | | | | — | | | | | | — | | | | | — |
| 3 (1.75 mmol/l) | 320 | | | | | | 292 | | | | | | 264 | | | | | | 264 |

(—: Recording was not available)

In spite of administering the taurine or 1-methionine as a bolus, the degree of vasodilatation, i.e. hypotension obtained with the used dosage was never excessive, and considered to be Just right for clinical purposes; it could be achieved with an isotonic solution as well. However the duration of such vaso-dilating and bradycardic effects needs further assessment to determine the best dosage and frequency of administration. Because of this moderate hypotensive effect, and the lack of cardio-toxic effects, monitoring is practically unnecessary. It can be given as a bolus as opposed to most other drugs used to induce hypotension acutely that need to be given as an intravenous drip therefore requiring close monitoring since the dose must be titrated to the response, which implies the need for personnel and equipment, that could be obviated with the present invention.

The hypotensive effects of 10 mmol/kg divided in 3 boluses were tabulated, because they were observations made concomitant to the underlying basic study of protection. The amount required for blood pressure control perioperatively, i.e. when used as a component of the anesthesia per se, only 1 to 3 mmol/kg are needed, and at this dosage it could be administered with impunity, without fearing untowards effects.

A similar vasodilating effect is obtained with even lesser amounts of 1-methionine (1 to 1.75 mmol/kg bolus, for a total of 3 mmol/kg given as a 4.5% or isotonic solution).

EXAMPLE 6

The blood flow effects of topical taurine solution to the dorsal aspect of the toes were examined by measuring skin temperature with an infra-red camera (thermography) in a patient (TAM) with frostbite of the left foot (4th toe being the worse, 1997), without and with iced cold water immersion challenge for 5 seconds. The skin temperature reflects the blood flow to the area, the warmer the greater blood flow (Tables 6A and 6B, data obtained in March, 1997).

TABLE 6A

| | Without iced-water challenge | | | | | |
|---|---|---|---|---|---|---|
| | TOE-SKIN TEMPERATURE | | | | | |
| | EVALUATION-SIDE | | | CONTRA-LATERAL SIDE | | |
| Room temp | Average 4* toes | | | Average 4* toes | | |
| 27.5 | (1,2,4,5)* | % of Max change | 3rd | (1,2,4,5)* | 3rd | |
| Baseline | 32.25 | | 31.4 | 31.85 | 31.5 | |
| | Topical-Taurine | | Nothing | Topical-Water | Nothing | |
| 5 mins | 33.02 | 81.05 | 32 | 31.67 | 31.9 | |
| 10 mins | 32.7 | 47.37 | 31.8 | 31.2 | 31.1 | |
| 15 mins | 32.9 | 68.4 | 32.3 | 31.37 | 31.8 | |
| 20 mins | 33.2 | 100 | 32.1 | 31.85 | 31.7 | |
| 25 mins | 33.02 | 81.05 | 32.1 | 31.37 | 31.7 | |
| 30 mins | 32.87 | 65.26 | 31.9 | 31.6 | 31.9 | | mins: minutes; secs: seconds; temp: temperature in Celsius.

TABLE 6B

Iced-water challenge

| Room temp 27.7 | Average 5 toes Evaluation side | Temp change | % Recovery | Average 5 toes Contra-lateral side | Temp change | % Recovery |
|---|---|---|---|---|---|---|
| Baseline | 32.62 | | | 31.92 | | |
| Iced water (5 secs) | 24.2 | 8.42 | | 21.56 | 10.36 | |
| | Topical Taurine | | | Topical water | | |
| 5 mins | 29.38 | | 61.52 | 26.58 | | 48.65 |
| 10 mins | 31.42 | | 85.75 | 28.16 | | 63.71 |
| 15 mins | 31.66 | | 88.6 | 28.6 | | 67.95 |
| 20 mins | 30.92 | | 79.81 | 28.06 | | 62.74 |
| 25 mins | 31.5 | | 86.7 | 28.16 | | 63.71 |
| 30 mins | 31.04 | | 79.81 | 27.46 | | 56.95 | mins: minutes; secs: seconds; temp: temperature in Celsius.

How fast the skin temperature returns to normal after a short period of immersion into iced-water is a commonly used clinical test to evaluate the blood flow to the area and its neurogenic control. The non-specific protective vasodilating effect exerted by the topically absorbed taurine will be manifested as increase of temperature, over the basal temperature or by accelerating the recovery of the basal temperature after iced-water immersion.

Accordingly as can be seen in the Tables 6A and 6B, topical 10% taurine increases the temperature of the toes where it was applied whether it is applied without (Table 6A) or with (Table 6B) prior challenge of exposure to cold. The maximal effects are seen between 15 to 20 minutes after its topical application in both situations. Though not tabulated, similar responses were observed with topically applied methionine solution.

Although not tabulated similar response of slightly lesser magnitude is observed when applied to normal subjects, not only on feet, but also on hands and the forehead. The implication being that it should be especially effective when applied to patients who have various degrees of neurovascular disorders.

Whether such vasodilating effects would have therapeutic value was explored in the same patient with frostbite, one year later. In 1998, the frostbite became symptomatic in both feet. Tables 7A and 7B summarizes the therapeutic effect of 5% taurine solution topically applied once daily after frostbite became symptomatic as the weather became colder. During the first week it was only applied to the left foot, the pain disappearing after 3 applications as substantiated by the improved thermographic data obtained after 5 applications of the topical solution consisting of the marked improvement of the % recovery 30 minutes after the iced water challenge (55.58% before VS 79.14% after taurine application). The right foot pain persisted unchanged during this time.

During the following week 5% taurine was topically applied to both feet. As it could be anticipated the therapeutic effects were more pronounced on the right or less affected foot; continued improvement was noted on the left foot as substantiated by the faster recovery than the previous week, although the extent of recovery remained the same.

Because the above therapeutic effects of topical application must be secondary to the vasodilatory effects, iso-osmolar concentration should suffice.

TABLE 7A

| | RIGHT FOOT TEMPERATURE | | | | | | | LEFT FOOT TEMPERATURE | | | | | | |
|---|---|---|---|---|---|---|---|---|---|---|---|---|---|---|
| DATE Toes | 1st | 2nd | 3rd | 4th | 5th | Average 1–5 | % Recovery | 1st | 2nd | 3rd | 4th | 5th | Average 1–5 | % Recovery |
| 97-1028 BASELINE before symptoms. Weather MAX = 20; MIN = 10–12 | | | | | | | | | | | | | | |
| Control | 29.6 | 27 | 26.2 | 26.6 | 27.8 | 27.44 | | 28.8 | 26.2 | 24.9 | 24.9 | 24.7 | 25.86 | |
| Iced-water Immersion (10 secs) | | | | | | | Temp. Diff. | | | | | | | Temp. Diff. |
| Post 0 mins | 22.9 | 19.6 | 17.1 | 16.4 | 18.3 | 18.86 | 8.58 | 21.6 | 16.9 | 16.2 | 15.6 | 17 | 17.46 | 8.4 |
| 5 mins | 25.5 | 22.4 | 20.3 | 20.4 | 21 | 21.92 | 35.66 | 24.4 | 19.9 | 19.8 | 20.5 | 19.6 | 20.84 | 40.24 |
| 10 mins | 25.1 | 22.6 | 22.9 | 20.8 | 21.1 | 22.1 | 37.76 | 23.8 | 19.9 | 19.9 | 19.8 | 19.4 | 20.56 | 36.95 |
| 15 mins | 25.2 | 23.1 | 21.4 | 20.9 | 21.4 | 22.4 | 41.26 | 24 | 21.2 | 20.2 | 20.2 | 20.2 | 21.16 | 44.05 |
| 20 mins | 24.5 | 23.4 | 21.8 | 21.3 | 21.7 | 22.54 | 42.9 | 24 | 21.4 | 20.2 | 20.3 | 20.4 | 21.26 | 45.24 |
| 25 mins | 25.1 | 23.9 | 21.9 | 21.7 | 21.7 | 22.86 | 46.62 | 26 | 21.7 | 20.4 | 20.5 | 20.5 | 21.82 | 51.91 |
| 30 mins | 24.3 | 23.2 | 21.6 | 21.3 | 21.2 | 22.32 | 40.33 | 26.4 | 21.6 | 20.2 | 20.1 | 20.3 | 22.075 | 55 |
| 98-0130 BEFORE RX: Symptomatic (pain and erythema of all toes) L = 25 days; R = 11 days. Weather MAX: 8; MIN: –1.0 | | | | | | | | | | | | | | |
| Control | 24.5 | 23.6 | 23.6 | 23.3 | 23.5 | 23.7 | | 24.6 | 24.8 | 24.4 | 23.5 | 23.6 | 24.18 | |
| Iced-water immersion (10 secs) | | | | | | | | | | | | | | |
| Post 0 mins | 15.8 | 14.9 | 16 | 13.9 | 14.1 | 14.94 | 8.76 | 16 | 15.4 | 14.9 | 14.9 | 14.9 | 15.22 | 8.96 |
| 5 mins | 20.4 | 19.3 | 18.3 | 18 | 19.1 | 19.02 | 46.58 | 20.3 | 19.4 | 19.3 | 18.7 | 19.2 | 19.38 | 46.43 |
| 10 mins | 20.6 | 19.9 | 18.7 | 18.7 | 19.4 | 19.46 | 51.6 | 20.9 | 19.8 | 18.7 | 19.4 | 19.7 | 19.7 | 50 |
| 15 mins | 20.7 | 20.1 | 18.7 | 19.1 | 19.5 | 19.62 | 53.42 | 20.7 | 20.2 | 19.1 | 19.8 | 19.9 | 19.94 | 52.68 |
| 20 mins | 20.2 | 20 | 18.4 | 18.8 | 19.1 | 19.3 | 49.77 | 20.4 | 20.4 | 18.8 | 19.5 | 19.4 | 19.7 | 50 |
| 25 mins | 20.3 | 19.9 | 18.5 | 18.8 | 19 | 19.3 | 49.77 | 20.8 | 21.1 | 19.1 | 19.6 | 19.6 | 20.04 | 53.8 |
| 30 mins | 19.9 | 19.7 | 18.3 | 18.6 | 18.7 | 19.04 | 46.8 | 20.9 | 21.6 | 19.4 | 19.6 | 19.5 | 20.2 | 55.58 |
| AFTER TOPICAL-TAURINE (5% solution) | | | | | | | | | | | | | | |
| 98-0206 L only (one week) (L pain subsided after 3 applications; with marked improvement of erythema; R unchanged): Weather: MAX: 12; MIN: 6 | | | | | | | | | | | | | | |
| Control | 26.8 | 26.7 | 26.3 | 26.4 | 26.7 | 28.58 | | 28.4 | 28 | 29 | 28.5 | 28 | 28.38 | |
| Iced-water immersion (10 secs) | | | | | | | | | | | | | | |
| Post 0 mins | 19.5 | 17.4 | 17 | 16.7 | 18.3 | 17.78 | 8.8 | 21.5 | 18.9 | 20.3 | 20 | 19.5 | 20.04 | 8.34 |
| 5 mins | 22.1 | 21.2 | 20.3 | 20.6 | 20.8 | 21 | 36.59 | 25.5 | 23.7 | 23.3 | 23.5 | 22.8 | 23.76 | 44.6 |
| 10 mins | 21.8 | 21.3 | 19.9 | 20.7 | 21.1 | 20.96 | 36.14 | 24.2 | 23.3 | 22.8 | 23.3 | 22.9 | 23.3 | 39.09 |
| 15 mins | 22.6 | 22.3 | 20.3 | 21.1 | 21.4 | 21.54 | 42.73 | 25.3 | 23 | 23.5 | 23.3 | 23.8 | 23.8 | 45.08 |
| 20 mins | 23.7 | 22.4 | 20.1 | 21 | 21.2 | 21.68 | 44.32 | 28.9 | 23.9 | 22.4 | 23.2 | 23 | 24.28 | 50.84 |
| 25 mins | 26.3 | 24.1 | 20.8 | 21.2 | 21.6 | 22.8 | 57.05 | 30.9 | 26.4 | 24.3 | 23.8 | 23.4 | 25.76 | 68.59 |
| 30 mins | 27.4 | 25.8 | 21.5 | 21.5 | 21.6 | 23.56 | 65.68 | 31.8 | 28.4 | 25.2 | 24.2 | 23.6 | 26.64 | 79.14 |
| 98-0213 L (2 weeks), R (one week: R pain subsided after 3 applications; with marked improvement of erythema); Weather: MAX: 13; MIN: 4 | | | | | | | | | | | | | | |
| Control | 32 | 30.9 | 31.3 | 30.4 | 30.1 | 30.94 | | 29.4 | 27.7 | 27.7 | 27.8 | 27.7 | 28.06 | |
| Iced-water immersion (10 secs) | | | | | | | | | | | | | | |
| Post 0 mins | 22.5 | 19.9 | 19 | 18.5 | 19.2 | 19.82 | 11.12 | 20.3 | 16.8 | 17.3 | 18.5 | 17.3 | 18.04 | 10.02 |
| 5 mins | 27.4 | 25.8 | 25.8 | 25.5 | 25 | 25.9 | 54.68 | 25.9 | 21.7 | 21.8 | 22.4 | 22.8 | 22.92 | 48.7 |
| 10 mins | 29.6 | 28.4 | 26.9 | 26.4 | 26 | 21.06 | 65.11 | 25.8 | 22.1 | 22 | 22.9 | 23.1 | 23.18 | 51.3 |
| 15 mins | 31.9 | 30.3 | 29.2 | 27.5 | 28.5 | 29.48 | 86.87 | 28.9 | 23 | 22.7 | 23.3 | 23.9 | 24.36 | 63.07 |
| 20 mins | 32.5 | 31.8 | 30.3 | 28.4 | 29.9 | 30.58 | 96.76 | 31.1 | 23.7 | 23 | 23.6 | 24.2 | 25.12 | 70.66 |
| 25 mins | 32.7 | 32.1 | 30.8 | 29.3 | 30.6 | 31.1 | 101.44 | 31.5 | 24.5 | 23.2 | 23.8 | 24 | 25.4 | 73.45 |
| 30 mins | 32.7 | 32.2 | 31 | 29.8 | 30.8 | 31.3 | 103.24 | 31.9 | 25.4 | 23.7 | 23.8 | 24.2 | 25.8 | 77.45 |

Temp. Diff: Temperature difference in Celsius; L = left foot; R = right foot; secs: seconds: mins: minutes.

REFERENCES

Benveniste H., Drejer J., Schousboe A., Diemer N. H. (1984): Elevation of extracellular concentrations of glutamate and aspartate in rat hippocampus during transient cerebral ischemia monitored by intracerebral microdialysis. J Neurochem 43: 1369–1374.

Choi D. W. (1990): Cerebral hypoxia: Some new approaches and unanswered questions. J Neurosc, 10: 2493–2501

DeLeo J., Toth L., Schubert P., Rudolphi K., Kreutzberg G. W. (1987): Ischemia-induced neuronal cell death, Calcium accumulation, and glial response in the hippocampus of the mongolian gerbil and protection by Propentofylline (HWA 285). J Cerebral Blood Flow and Metabolism 7: 745–751.

Fariello R. G., Golden G. T., Pisa M. (1982): Homotaurine (3 aminopropanesulfonic acid; 3 APS) protects from the convulsant and cytoytoxic effects of systemically administered kainic acid. Neurology 32: 241–245.

Faulconer A., and Bickford R. G. (1960): Electroencephalography in Anesthesiology. Springfield, III. Charles C. Thomas, Publisher. pp: 6–18.

Fredholm B. B. (1995): Adenosine receptors in the central nervous system. News in Physiological Sciences (NIPS), 10: 122–128.

Fukunaga A., Miyamoto A. T., Kikuta Y., Kaneko Y., Ichinohe T. (1995): Role of adenosine and adenosine triphosphate as anesthetic adjuvants. In: Adenosine and adenine nucleotides: From molecular biology to integrative physiology. Ed Belardinelli L., Pelleg A. Boston, Dordrecht, London: Kluwer Academic Publishers. pp: 511–523.

Goldberg M. P., Monyer H., Weiss J. W., Choi D. W. (1988): Adenosine reduces cortical neuronal injury induced by oxygen or glucose deprivation in vitro. Neurosci Lett. 89: 323–7, Hillered L., Hallstrom A., Segersvard S., Persson L., Ungerstedt (1989): Dynamics of extracellular metabolites in the striatun after middle cerebral artery occlusion in the rat monitored by intracerebral microdialysis. J Cereb Blood Flow Metab 9: 607–616.

Huxtable R. J. (1980): Insights on functions: Metabolism and pharmacology of Taurine in the brain. In the role of peptides andaminoacids as neurotransmitters. Ed Lombardini J. B., Kenny A. D. New York, Alan R. Liss, Inc pp 53–97.

Jacobson M. A., (1995): Molecular Biology of Adenosine Receptors, In Adenosine and Adenine Nucleotides: From molecular biology to integrative physiology. Ed Belardinelli L, Pelleg A. Boston, Dordrecht, London: Kluwer Academic Publishers. pp: 5–13.

Johnson J. W., Ascher P. (1987): Glycine potentiates the NMDA response in cultured mouse brain neurons. Nature, 325: 529–531.

Kato H., Araki T., Kogure K. (1990): Role of the Excitotoxic mechanism in the development of neuronal damage following repeated brief cerebral ischemia in the gerbil: protective effects of MK-801 and pentobarbital. Brain Research 616: 175–179.

Lehmann A., Hagberg H., Hamberger A. (1984): A role for Taurine in the maintenance of homeostasis in the central nervous system during hyperexcitation? Neuroscience Letters 52: 341–346.

Lloyd H. G. E., Deussen A., Wuppermann H., Schrader J. (1988): The transmethylation pathway as a source for adenosine in the isolated guinea-pig heart. Biochem J, 252: 489–494.

McDonald J. W., Silverstein F. S., Cardona D., Hudson C., Chen R., Johnston M. V. (1990): Systemic administration of MK-801 protects against N-methyl-D-aspartate- and quisqualate-mediated neurotoxicity in perinatal rats. Neuroscience 36: 589–599.

Michenfelder J. D. (a) (1988): Anesthesia and the Brain. Protecting the brain. New York, Edinbutrgh, London, Melbourne. Churchill Livingstone, pp: 181–193.

Michenfelder J. D. (b) (1988): Anesthesia and the Brain. Assessing the brain. New York, Edinbutrgh, London, Melbourne. Churchill Livingstone, pp: 169–180.

Nilsson P., Hillered L., Ponten U., Ungerstedt U. (1990): Changes in cortical extracellular levels of energy-related metabolites and amino-acids following concussive brain injury in rats. J Cereb Blood Flow Metab 10: 631–637.

Persson L., Hillered L. (1992): Chemical monitoring of neurosurgical intensive care patients using intracerebral microdialysis. J Neurosurg 76: 72–80.

Rothman S. M., Olney J. W. (1986): Glutamate and the pathophysiology of hypoxic-ischemic brain damage. Ann Neurol 19: 105–111.

Rudolphi K. A., Schubert P., Parkinson F., and Fredholm B. B. (1992): Cerebrovascular and Brain Metabolism Reviews. Raven Press, Ltd, NY, 4: 346–369.

Schrader J. (1991): Formation and metabolism of adenosine and adenine nucleotides in cardiac tissue. In Adenosine and Adenine nucleotides as regulators of cellular function. Ed. Phillis J. W. CRC Press, Boca Raton, Ann Arbor, Boston, London. pp 56–65.

Schubert P., Kreutzberg G. W. (1993): Cerebral protection by adenosine. Acta Neurochirur (Suppl) 57: 80–88.

Simpson R. E., O'Regan M. H., Perkins L. M., Phillis J. W. (1992): Excitatory aminoacid release from the ischemic rat cerebral cortex: Effects of adenosine receptor agonists and antagonists. J Neurochem 58: 1683–1690.

Sollevi A. (1992): Adenosine infusion during isofluorenenitrous oxide anesthesia: indications of perioperative analgesic effect, Acta Anaesthesiol Scand 36: 595–599.

Stone T. W. (1981): The effects of morphine and methionine-enkephalin on the release of purines from cerebral cortex slices of rats and mice. Br J Pharmacol 74: 171–176.

van Gelder N. M. (a) (1972): Antagonism by taurine of cobalt induced epilepsy in cat and mouse. Brain Research 47: 157–165.

van Gelder N. M. (b) (1977): Taurine treatment of spontaneous chronic epilepsy in a cat. Epilepsia 18: 45–54.

Van Wylen D. G. L., Park T. S., Rubio R., Berne R. M. (1986): Increases in cerebral interstitial fluid adenosine concentration during hypoxia, local potassium infusion, and ischemia. J Cereb Blood Flow Metab 6: 522–528.

Wieloch T., Siesjo B. K. (1982): Ischemic brain injury: the importance of Calcium, lipolytic activities, and free fatty acids. Path. Biol. 5: 269–277.

Wright C. E. (1986): Taurine: Biological update. Ann Rev Biochem 55: 427–53.

What is claimed is:

1. A method of treating or preventing ischemic injury of mammalian tissues, consisting essentially of intravenously administering to a mammal in need thereof a therapeutically effective amount of a hypertonic solution containing at least one compound selected from the group consisting of taurine, homotaurine, and 1-methionine.

2. The method of claim 1, wherein said ischemic injury is in the central nervous system.

3. The method of claim 1, consisting essentially of administering said compound at a loading dose of 6–10 mmol/kg of body weight.

4. The method of claim 1, consisting essentially of administering a hypertonic solution containing at least 5% by weight of taurine.

5. The method of claim 1, consisting essentially of administering taurine in combination with 1-methionine.

6. The method of claim 1, wherein said hypertonic solution further contains a supplementary protective coadjuvant.

7. The method of claim 1, wherein said hypertonic solution further contains at least one selected from adenine nucleosides, nucleotides, mannitol, vitamin C, glutathione, vitamin E, magnesium, dantrolene, corticosteroids, promazine, nicholin, 21-amino steroids, non-steroidal anti-inflammatory agents, calcium antagonists, and $K_{ATP}$ channel openers.

8. The method of claim 7, wherein said $K_{ATP}$ channel openers are selected from the group consisting of pinacidil, nicorandil, and chromakalim.

9. The method of claim 1, wherein said hypertonic solution further contains mannitol.

10. The method of claim 1, wherein said compound is taurine.

11. The method of claim 1, wherein said compound is homotaurine.

12. The method of claim 1, wherein said compound is 1-methionine.

* * * * *